United States Patent [19]
Staunton et al.

[11] Patent Number: 5,922,570
[45] Date of Patent: Jul. 13, 1999

[54] CYTOPLASMIC MODULATORS OF INTEGRIN BINDING/SIGNALLING

[75] Inventors: Donald E. Staunton, Kirkland; Edith Salot Harris, Seattle, both of Wash.

[73] Assignee: ICOS Corporation, Bothell, Wash.

[21] Appl. No.: 08/583,562

[22] Filed: Jan. 5, 1996

[51] Int. Cl.⁶ ................................................. C12P 21/06
[52] U.S. Cl. ................. 435/69.2; 435/320.1; 435/325; 536/23.5; 530/353
[58] Field of Search .................. 536/23.5; 435/69.2, 435/320.1, 325; 530/353

[56] References Cited

U.S. PATENT DOCUMENTS 5,506,126  4/1996  Seed et al. .

OTHER PUBLICATIONS

Baker et al. The Study of Biology, 4th edition, p. 9, Addison–Wesley Publishing, Jan. 1982.
Altin et al., "A One–Step Procedure for Biotinylation and Chemical Cross–Linking of Lymphocyte Surface and Intracellular Membrane–Associated Molecules," *Anal. Biochem.* 224:382–389 (1995).
Arnaout, Amin M., "Structure and Function of the Leukocyte Adhesion Molecules CD11/CD18," *Blood* 75(5):1037–1050 (1990).
Baron et al. "The Pathogenesis of Adoptive Murine Autoimmune Diabetes Requires an Interaction between α4–Integrins and Vascular Cell Adhesion Molecule–1," *J. Clin. Invest.* 93:1700–1708 (1994).
Baron et al. "Surface Expression of α4 Integrin by CD4 T Cells Is Required for Their Entry into Brain Parenchyma," *J. Exp. Med.* 177:57–68 (1993).
Burkly et al., "Protection Against Adoptive Transfer of Autoimmune Diabetes Mediated Through Very Late Antigen–4 Integrin," *Diabetes* 43:529–534 (1994).
Clark and Brugge, "Integrins and Signal Transduction Pathways" The Road Taken, *Science* 268:233–239 (1995).
Cunningham et al., "Actin–Binding Protein Requirement for Cortical Stability and Efficient Locomotion," *Science* 255:325–327 (1992).
Durfee et al., "The Retinoblastoma Protein Associates with the Protein Phosphatase Type 1 Catalytic Subunit," *Genes & Development* 7:555–569 ((1993).
Ezzell et al., "Localization of the Domain of Actin–binding Protein That Binds to Membrane Glycoprotein Ib and Actin in Human Platelets," *J. Biol. Chem.* 263(26):13302–13309 (1988).
Ferguson et al., "Antigen–Independent Processes in Antigen–Specific Immunity," *J. Immunol.* 150(4):1172–1182 (1993).
Gorlin et al., "Human Endothelial Actin–binding Protein (ABP–280, Nonmuscle Filamin): A Molecular Leaf Spring," *J. Cell Biol.* 111:1089–1105 (1990).
Gumbiner et al., "Proteins Associated with the Cytoplasmic Surface of Adhesion Molecules," *Neuron* 11:551–564 (1993).
Hemler et al., "Structure of the Integrin VLA–4 and its Cell–Cell and Cell–Matrix Adhesion Functions," *Immunol Rev.* 114:45–60 (1990).
Jutila, Mark A., "Function and Regulation of Leukocyte Homing Receptors," *J. Leukocyte Biol.* 55:133–140 (1994).
Kilshaw et al. "A New Surface Antigen on Intraepithelial Lymphocytes in the Intestine," *Eur. J. Immunol.* 20:2201–2207 (1990).
Kishimoto et al., "Cloning of the β Subunit of the Leukocyte Adhesion Proteins: Homology to an Extracellular Matrix Receptor Defines a Novel Supergene Family," *Cell* 48:681–690 (1987).
LaFlamme et al., "Regulation of Fibronectin Receptor Distribution," *J. Cell Biol.* 117(2):437–447 (1992).
Lazarovits et al., "Differential Expression in Rheumatoid Synovium and Synovial Fluid of α4β7 Integrin," *J. Immunol.* 151(11):6482–6489 (1993).
Leedman et al., "Cloning from the Thyroid of a Protein Related to Actin Binding Protein that is Recognized by Graves Disease Immunoglobulins," *Proc. Natl. Acad. Sci.* 90:5994–5998 (1993).
Lobb and Hemler, "The Pathophysiologic Role of α4 Integrins In Vivo," *J. Clin. Invest.* 94:1722–1728 (1994).
McEver, Rodger P., "Leukocyte–Endothelial Cell Interactions," *Curr. Opin. Cell. Biol.* 4:840–849 (1992).
Milne and Piper, "The Role of the VLA–4 Integrin in a Model of Airway Inflammation in the Guinea–Pig," *Br. J. Pharmacol* 112:82P (Abstr) (1994).
Miyamoto et al., "Synergistic Roles for Receptor Occupancy and Aggregation in Integrin Transmembrane Function," *Science* 267:883–835 (1995).
Mulligan et al., "Role of $\alpha_1$, $\beta_2$ Integrins and ICAM–1 in Lung Injury after Deposition of IgG and IgA Immune Complexes," *J. Immunol.* 150(6):2407–2417 (1993a).
Mulligan et al., "Requirements for Leukocyte Adhesion Molecules in Nephrotoxic Nephritis," *J. Clin. Invest.* 91:577–587 (1993b).
Nakajima et al., "Role of Vascular Cell Adhesion Molecule 1/Very Late Activation Antigen 4 and Intercellular Adhesion Molecule 1/Lymphocyte Function–associated Antigen 1 Interactions in Antigen–induced Eosinophil and T Cell Recruitment into the Tissue," *J. Exp. Med.* 179:1145–1154 (1994).

(List continued on next page.)

*Primary Examiner*— Christina Chan
*Assistant Examiner*—Patrick J. Nolan
*Attorney, Agent, or Firm*—Marshall, O'Toole, Gerstein, Murray & Borun

[57] ABSTRACT

The present invention relates to purified and isolated polynucleotides encoding a polypeptide which specifically bind to a cytoplasmic portion of an integrin. Specifically, the invention provides a FLP-1-encoding polynucleotide and the polypeptide product of the gene. Expression vectors comprising the polynucleotide, antibodies which recognize the polypeptide, hybridomas which secrete the antibodies, and method to identify modulators of interaction of the polypeptide with $\beta_7$ subunits sequences are also provided.

8 Claims, No Drawings

OTHER PUBLICATIONS

Paul et al., "The Efficacy of LFA–1 and VLA–4 Antibody Treatment in Rat Vascularized Cardiac Allograft Rejection," *Transplantation*, 55(5):1196–1199 (1993).

Pavalko et al., "Role of Adhesion Molecule Cytoplasmic Domains in Mediating Interactions with the Cytoskeleton," *Proc. Soc. Exp. Biol. Med.*, 205:282–293, 1994.

Podolsky et al., "Attenuation of Colitis in the Cotton–top Tamarin by Anti–α4 integrin Monoclonal Antibody," *J. Clin. Invest.* 92:372–380 (1993).

Pretolani et al., "Antibody to Very Late Activation Antigen 4 Prevents Antigen–induced Bronchial Hyperactivity and Cellular Infiltration in the Guinea Pig Airways," *J. Exp. Med.* 180:795–805 (1994).

Schweighoffer et al., "Selective Expression of Integrin α4β7 on a Subset of Human CD4+ Memory T Cells with hallmarks of Gut–Trophism," *J. Immunol.* 151(2):717–729 (1993).

Sharma et al., "Direct Interaction of Filamin (ABP–280) with the β2–Integrin Subunit CD18," *J. Immunol.* 154:3461–3470 (1995).

Springer et al., "Traffic Signals for Lymphocyte Recirculation and Leukocyte Emigration: The Multistep Paradigm," *Cell* 76:301–314 (1994).

Van der Vireen et al., "A Novel Leukointegrin, αdβ2, Binds Preferentially to ICAM–3," *Immunity* 3:683–690 (1995).

Weg et al., "A Monoclonal Antibody Recognizing Very Late Activation Antigen–4 Inhibits Eosinophil Accumulation In Vivo," *J. Exp. Med.* 177:561–566 (1993).

Winn and Harlan, "CD18–Independent Neutrophil and Mononuclear Leukocyte Emigration into the Peritoneum of Rabbits," *J. Clin. Invest.* 92:1168–1173 (1993).

Yang et al., "Inhibition of Insulitis and Prevention of Diabetes in Nonobese Diabetic Mice by Blocking L–selectin and Very Late Antigen 4 Adhesion Receptors," *Proc. Natl. Acad. Sci. USA* 90:10494–10498 (1993).

Yednock et al., "Prevention of Experimental Autoimmune Encephalomyelitis by Antibodies Against α4β1 Integrin," *Nature* 356:63–66 (1992).

SEQUENCE LISTING (1) GENERAL INFORMATION:

(iii) NUMBER OF SEQUENCES: 36

(2) INFORMATION FOR SEQ ID NO:1:

(i) SEQUENCE CHARACTERISTICS:
      (A) LENGTH: 2574 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 1..2574

(xi) SEQUENCE DESCRIPTION: SEQ ID NO:1:

```
CCT TTT GAC CTG GTC ATT CCG TTT GCT GTC AGG AAA GGA GAA ATC ACT        48
Pro Phe Asp Leu Val Ile Pro Phe Ala Val Arg Lys Gly Glu Ile Thr
 1               5                  10                  15

GGA GAG GTC CAC ATG CCT TCT GGG AAG ACA GCC ACA CCT GAG ATT GTG        96
Gly Glu Val His Met Pro Ser Gly Lys Thr Ala Thr Pro Glu Ile Val
             20                  25                  30

GAC AAC AAG GAC GGC ACG GTC ACT GTT AGA TAT GCC CCC ACT GAG GTC       144
Asp Asn Lys Asp Gly Thr Val Thr Val Arg Tyr Ala Pro Thr Glu Val
         35                  40                  45

GGG CTC CAT GAG ATG CAC ATC AAA TAC ATG GGC AGC CAC ATC CCT GAG       192
Gly Leu His Glu Met His Ile Lys Tyr Met Gly Ser His Ile Pro Glu
     50                  55                  60

AGC CCA CTC CAG TTC TAC GTG AAC TAC CCC AAC AGT GGA AGT GTT TCT       240
Ser Pro Leu Gln Phe Tyr Val Asn Tyr Pro Asn Ser Gly Ser Val Ser
 65                  70                  75                  80
```

-continued

| | | |
|---|---|---|
| GCA TAC GGT CCA GGC CTC GTG TAT GGA GTG GCC AAC AAA ACT GCC ACC<br>Ala Tyr Gly Pro Gly Leu Val Tyr Gly Val Ala Asn Lys Thr Ala Thr<br>                  85                        90                      95 | 288 |
| TTC ACC ATC GTC ACA GAG GAT GCA GGA GAA GGT GGT CTG GAC TTG GCT<br>Phe Thr Ile Val Thr Glu Asp Ala Gly Glu Gly Gly Leu Asp Leu Ala<br>                 100                    105                     110 | 336 |
| ATT GAG GGC CCC TCA AAA GCA GAA ATC AGC TGC ATT GAC AAT AAA GAT<br>Ile Glu Gly Pro Ser Lys Ala Glu Ile Ser Cys Ile Asp Asn Lys Asp<br>         115                      120                      125 | 384 |
| GGG ACA TGC ACA GTG ACC TAC CTG CCG ACT CTG CCA GGC GAC TAC AGC<br>Gly Thr Cys Thr Val Thr Tyr Leu Pro Thr Leu Pro Gly Asp Tyr Ser<br>130                       135                      140 | 432 |
| ATT CTG GTC AAG TAC AAT GAC AAG CAC ATC CCT GGC AGC CCC TTC ACA<br>Ile Leu Val Lys Tyr Asn Asp Lys His Ile Pro Gly Ser Pro Phe Thr<br>145                       150                     155               160 | 480 |
| GCC AAG ATC ACA GAT GAC AGC AGG CGG TGC TCC CAG GTG AAG TTG GGC<br>Ala Lys Ile Thr Asp Asp Ser Arg Arg Cys Ser Gln Val Lys Leu Gly<br>                 165                    170                     175 | 528 |
| TCA GCC GCT GAC TTC CTG CTC GAC ATC AGT GAG ACT GAC CTC AGC AGC<br>Ser Ala Ala Asp Phe Leu Leu Asp Ile Ser Glu Thr Asp Leu Ser Ser<br>                 180                    185                     190 | 576 |
| CTG ACG GCC AGC ATT AAG GCC CCA TCT GGC CGA GAC GAG CCC TGT CTC<br>Leu Thr Ala Ser Ile Lys Ala Pro Ser Gly Arg Asp Glu Pro Cys Leu<br>         195                      200                      205 | 624 |
| CTG AAG AGG CTG CCC AAC AAC CAC ATT GGC ATC TCC TTC ATC CCC CGG<br>Leu Lys Arg Leu Pro Asn Asn His Ile Gly Ile Ser Phe Ile Pro Arg<br>210                       215                     220 | 672 |
| GAA GTG GGC GAA CAT CTG GTC AGC ATC AAG AAA AAT GGC AAC CAT GTG<br>Glu Val Gly Glu His Leu Val Ser Ile Lys Lys Asn Gly Asn His Val<br>225                       230                     235                   240 | 720 |
| GCC AAC AGC CCC GTG TCT ATC ATG GTG GTC CAG TCG GAG ATT GGT GAC<br>Ala Asn Ser Pro Val Ser Ile Met Val Val Gln Ser Glu Ile Gly Asp<br>                 245                    250                     255 | 768 |
| GCC CGC CGA GCC AAA GTC TAT GGC CGC GGC CTG TCA GAA GGC CGG ACT<br>Ala Arg Arg Ala Lys Val Tyr Gly Arg Gly Leu Ser Glu Gly Arg Thr<br>                    260                     265                   270 | 816 |
| TTC GAG ATG TCT GAC TTC ATC GTG GAC ACA AGG GAT GCA GGT TAT GGT<br>Phe Glu Met Ser Asp Phe Ile Val Asp Thr Arg Asp Ala Gly Tyr Gly<br>                 275                    280                   285 | 864 |
| GGC ATA TCC TTG GCG GTG GAA GGC CCC AGC AAA GTG GAC ATC CAG ACG<br>Gly Ile Ser Leu Ala Val Glu Gly Pro Ser Lys Val Asp Ile Gln Thr<br>         290                      295                     300 | 912 |
| GAG GAC CTG GAA GAT GGC ACC TGC AAA GTC TCC TAC TTC CCT ACC GTG<br>Glu Asp Leu Glu Asp Gly Thr Cys Lys Val Ser Tyr Phe Pro Thr Val<br>305                       310                     315                   320 | 960 |
| CCT GGG GTT TAT ATC GTC TCC ACC AAA TTC GCT GAC GAG CAC GTG CCT<br>Pro Gly Val Tyr Ile Val Ser Thr Lys Phe Ala Asp Glu His Val Pro<br>                 325                    330                     335 | 1008 |
| GGG AGC CCA TTT ACC GTG AAG ATC AGT GGG GAG GGA AGA GTC AAA GAG<br>Gly Ser Pro Phe Thr Val Lys Ile Ser Gly Glu Gly Arg Val Lys Glu<br>                    340                     345                   350 | 1056 |
| AGC ATC ACC CGC ACC AGT CGG GCC CCG TCC GTG GCC ACT GTC GGG AGC<br>Ser Ile Thr Arg Thr Ser Arg Ala Pro Ser Val Ala Thr Val Gly Ser<br>                 355                    360                   365 | 1104 |
| ATT TGT GAC CTG AAC CTG AAA ATC CCA GAA ATC AAC AGC AGT GAT ATG<br>Ile Cys Asp Leu Asn Leu Lys Ile Pro Glu Ile Asn Ser Ser Asp Met<br>370                       375                     380 | 1152 |
| TCG GCC CAC GTC ACC AGC CCC TCT GGC CGT GTG ACT GAG GCA GAG ATT<br>Ser Ala His Val Thr Ser Pro Ser Gly Arg Val Thr Glu Ala Glu Ile<br>385                       390                     395               400 | 1200 |

| | |
|---|---|
| GTG CCC ATG GGG AAG AAC TCA CAC TGC GTC CGG TTT GTG CCC CAG GAG<br>Val Pro Met Gly Lys Asn Ser His Cys Val Arg Phe Val Pro Gln Glu<br>                      405                      410                      415 | 1248 |
| ATG GGC GTG CAC ACG GTC AGC GTC AAG TAC CGT GGG CAG CAC GTC ACC<br>Met Gly Val His Thr Val Ser Val Lys Tyr Arg Gly Gln His Val Thr<br>                      420                      425                      430 | 1296 |
| GGC AGC CCC TTC CAG TTC ACC GTG GGG GCA CTT GGT GAA GGA GGC GCC<br>Gly Ser Pro Phe Gln Phe Thr Val Gly Ala Leu Gly Glu Gly Gly Ala<br>                      435                      440                      445 | 1344 |
| CAC AAG GTG CGG GCA GGA GGC CCT GGC CTG GAG AGA GGA GAA GCG GGA<br>His Lys Val Arg Ala Gly Gly Pro Gly Leu Glu Arg Gly Glu Ala Gly<br>450                                455                      460 | 1392 |
| GTC CCA GCT GAG TTC AGC ATT TGG ACC CGG GAA GCA GGC GCT GGA GGC<br>Val Pro Ala Glu Phe Ser Ile Trp Thr Arg Glu Ala Gly Ala Gly Gly<br>465                                470                      475                      480 | 1440 |
| CTC TCC ATC GCT GTT GAG GGC CCC AGT AAG GCC GAG ATT ACA TTC GAT<br>Leu Ser Ile Ala Val Glu Gly Pro Ser Lys Ala Glu Ile Thr Phe Asp<br>                      485                      490                      495 | 1488 |
| GAC CAT AAA AAT GGG TCG TGC GGT GTA TCT TAT ATT GCC CAA GAG CCT<br>Asp His Lys Asn Gly Ser Cys Gly Val Ser Tyr Ile Ala Gln Glu Pro<br>                      500                      505                      510 | 1536 |
| GGT AAC TAC GAG GTG TCC ATC AAG TTC AAT GAT GAG CAC ATC CCG GAA<br>Gly Asn Tyr Glu Val Ser Ile Lys Phe Asn Asp Glu His Ile Pro Glu<br>                      515                      520                      525 | 1584 |
| AGC CCC TAC CTG GTG CCG GTC ATC GCA CCC TCC GAC GAC GCC CGC CGC<br>Ser Pro Tyr Leu Val Pro Val Ile Ala Pro Ser Asp Asp Ala Arg Arg<br>                      530                      535                      540 | 1632 |
| CTC ACT GTT ATG AGC CTT CAG GAA TCG GGA TTA AAA GTT AAC CAG CCA<br>Leu Thr Val Met Ser Leu Gln Glu Ser Gly Leu Lys Val Asn Gln Pro<br>545                                550                      555                      560 | 1680 |
| GCA TCC TTT GCT ATA AGG TTG AAT GGC GCA AAA GGC AAG ATT GAT GCA<br>Ala Ser Phe Ala Ile Arg Leu Asn Gly Ala Lys Gly Lys Ile Asp Ala<br>                      565                      570                      575 | 1728 |
| AAG GTG CAC AGC CCC TCT GGA GCC GTG GAG GAG TGC CAC GTG TCT GAG<br>Lys Val His Ser Pro Ser Gly Ala Val Glu Glu Cys His Val Ser Glu<br>                      580                      585                      590 | 1776 |
| CTG GAG CCA GAT AAG TAT GCT GTT CGC TTC ATC CCT CAT GAG AAT GGT<br>Leu Glu Pro Asp Lys Tyr Ala Val Arg Phe Ile Pro His Glu Asn Gly<br>                      595                      600                      605 | 1824 |
| GTC CAC ACC ATC GAT GTC AAG TTC AAT GGG AGC CAC GTG GTT GGA AGC<br>Val His Thr Ile Asp Val Lys Phe Asn Gly Ser His Val Val Gly Ser<br>610                                615                      620 | 1872 |
| CCC TTC AAA GTG CGC GTT GGG GAG CCT GGA CAA GCG GGG AAC CCT GCC<br>Pro Phe Lys Val Arg Val Gly Glu Pro Gly Gln Ala Gly Asn Pro Ala<br>625                                630                      635                      640 | 1920 |
| CTG GTG TCC GCC TAT GGC ACG GGA CTC GAA GGG GGN ACC ACA GGT ATC<br>Leu Val Ser Ala Tyr Gly Thr Gly Leu Glu Gly Xaa Thr Thr Gly Ile<br>                      645                      650                      655 | 1968 |
| CAG TCG GAA TTC TTT ATT AAC ACC ACC CGA GCA GGT CCA GGG ACA TTA<br>Gln Ser Glu Phe Phe Ile Asn Thr Thr Arg Ala Gly Pro Gly Thr Leu<br>                      660                      665                      670 | 2016 |
| TCC GTC ACC ATC GAA GGC CCA TCC AAG GTT AAA ATG GAT TGC CAG GAA<br>Ser Val Thr Ile Glu Gly Pro Ser Lys Val Lys Met Asp Cys Gln Glu<br>                      675                      680                      685 | 2064 |
| ACA CCT GAA GGG TAC AAA GTC ATG TAC ACC CCC ATG GCT CCT GGT AAC<br>Thr Pro Glu Gly Tyr Lys Val Met Tyr Thr Pro Met Ala Pro Gly Asn<br>                      690                      695                      700 | 2112 |
| TAC CTG ATC AGT GTC AAA TAC GGT GGG CCC AAC CAC ATC GTG GGC AGT<br>Tyr Leu Ile Ser Val Lys Tyr Gly Gly Pro Asn His Ile Val Gly Ser<br>705                                710                      715                      720 | 2160 |

```
CCC TTC AAG GCC AAG GTG ACT GGC CAG CGT CTA GTT AGC CCT GGC TCA        2208
Pro Phe Lys Ala Lys Val Thr Gly Gln Arg Leu Val Ser Pro Gly Ser
            725                 730                 735

GCC AAC GAG ACC TCA TCC ATC CTG GTG GAG TCA GTG ACC AGG TCG TCT        2256
Ala Asn Glu Thr Ser Ser Ile Leu Val Glu Ser Val Thr Arg Ser Ser
        740                 745                 750

ACA GAG ACC TGC TAT AGC GCC ATT CCC AAG GCA TCC TCG GAC GCC AGC        2304
Thr Glu Thr Cys Tyr Ser Ala Ile Pro Lys Ala Ser Ser Asp Ala Ser
        755                 760                 765

AAG GTG ACC TCT AAG GGG GCA GGG CTC TCA AAG GCC TTT GTG GGC CAG        2352
Lys Val Thr Ser Lys Gly Ala Gly Leu Ser Lys Ala Phe Val Gly Gln
770                 775                 780

AAG AGT TCC TTC CTG GTG GAC TGC AGC AAA GCT GGC TCC AAC ATG CTG        2400
Lys Ser Ser Phe Leu Val Asp Cys Ser Lys Ala Gly Ser Asn Met Leu
785                 790                 795                 800

CTG ATC GGG GTC CAT GGG CCC ACC ACC CCC TGC GAG GAG GTC TCC ATG        2448
Leu Ile Gly Val His Gly Pro Thr Thr Pro Cys Glu Glu Val Ser Met
            805                 810                 815

AAG CAT GTA GGC AAC CAG CAA TAC AAC GTC ACA TAC GTC GTC AAG GAG        2496
Lys His Val Gly Asn Gln Gln Tyr Asn Val Thr Tyr Val Val Lys Glu
            820                 825                 830

AGG GGC GAT TAT GTG CTG GCT GTG AAG TGG GGG GAG GAA CAC ATC CCT        2544
Arg Gly Asp Tyr Val Leu Ala Val Lys Trp Gly Glu Glu His Ile Pro
            835                 840                 845

GGC AGC CCT TTT CAT GTC ACA GTG CCT TAA                                2574
Gly Ser Pro Phe His Val Thr Val Pro Tyr
850                 855
```

(2) INFORMATION FOR SEQ ID NO:2:

(i) SEQUENCE CHARACTERISTICS:
        (A) LENGTH: 858 amino acids
        (B) TYPE: amino acid
        (D) TOPOLOGY: linear (ii) MOLECULE TYPE: protein (xi) SEQUENCE DESCRIPTION: SEQ ID NO:2:

```
Pro Phe Asp Leu Val Ile Pro Phe Ala Val Arg Lys Gly Glu Ile Thr
1               5                   10                  15

Gly Glu Val His Met Pro Ser Gly Lys Thr Ala Thr Pro Glu Ile Val
                20                  25                  30

Asp Asn Lys Asp Gly Thr Val Thr Val Arg Tyr Ala Pro Thr Glu Val
            35                  40                  45

Gly Leu His Glu Met His Ile Lys Tyr Met Gly Ser His Ile Pro Glu
        50                  55                  60

Ser Pro Leu Gln Phe Tyr Val Asn Tyr Pro Asn Ser Gly Ser Val Ser
65                  70                  75                  80

Ala Tyr Gly Pro Gly Leu Val Tyr Gly Val Ala Asn Lys Thr Ala Thr
                85                  90                  95

Phe Thr Ile Val Thr Glu Asp Ala Gly Glu Gly Gly Leu Asp Leu Ala
                100                 105                 110

Ile Glu Gly Pro Ser Lys Ala Glu Ile Ser Cys Ile Asp Asn Lys Asp
            115                 120                 125

Gly Thr Cys Thr Val Thr Tyr Leu Pro Thr Leu Pro Gly Asp Tyr Ser
        130                 135                 140

Ile Leu Val Lys Tyr Asn Asp Lys His Ile Pro Gly Ser Pro Phe Thr
145                 150                 155                 160

Ala Lys Ile Thr Asp Asp Ser Arg Arg Cys Ser Gln Val Lys Leu Gly
                165                 170                 175
```

-continued

```
Ser Ala Ala Asp Phe Leu Leu Asp Ile Ser Glu Thr Asp Leu Ser Ser
            180                 185                 190

Leu Thr Ala Ser Ile Lys Ala Pro Ser Gly Arg Asp Glu Pro Cys Leu
            195                 200                 205

Leu Lys Arg Leu Pro Asn Asn His Ile Gly Ile Ser Phe Ile Pro Arg
            210                 215                 220

Glu Val Gly Glu His Leu Val Ser Ile Lys Lys Asn Gly Asn His Val
225                 230                 235                 240

Ala Asn Ser Pro Val Ser Ile Met Val Val Gln Ser Glu Ile Gly Asp
            245                 250                 255

Ala Arg Arg Ala Lys Val Tyr Gly Arg Gly Leu Ser Glu Gly Arg Thr
            260                 265                 270

Phe Glu Met Ser Asp Phe Ile Val Asp Thr Arg Asp Ala Gly Tyr Gly
            275                 280                 285

Gly Ile Ser Leu Ala Val Glu Gly Pro Ser Lys Val Asp Ile Gln Thr
            290                 295                 300

Glu Asp Leu Glu Asp Gly Thr Cys Lys Val Ser Tyr Phe Pro Thr Val
305                 310                 315                 320

Pro Gly Val Tyr Ile Val Ser Thr Lys Phe Ala Asp Glu His Val Pro
            325                 330                 335

Gly Ser Pro Phe Thr Val Lys Ile Ser Gly Gly Arg Val Lys Glu
            340                 345                 350

Ser Ile Thr Arg Thr Ser Arg Ala Pro Ser Val Ala Thr Val Gly Ser
            355                 360                 365

Ile Cys Asp Leu Asn Leu Lys Ile Pro Glu Ile Asn Ser Ser Asp Met
370                 375                 380

Ser Ala His Val Thr Ser Pro Ser Gly Arg Val Thr Glu Ala Glu Ile
385                 390                 395                 400

Val Pro Met Gly Lys Asn Ser His Cys Val Arg Phe Val Pro Gln Glu
            405                 410                 415

Met Gly Val His Thr Val Ser Val Lys Tyr Arg Gly Gln His Val Thr
            420                 425                 430

Gly Ser Pro Phe Gln Phe Thr Val Gly Ala Leu Gly Glu Gly Gly Ala
            435                 440                 445

His Lys Val Arg Ala Gly Gly Pro Gly Leu Glu Arg Gly Glu Ala Gly
            450                 455                 460

Val Pro Ala Glu Phe Ser Ile Trp Thr Arg Glu Ala Gly Ala Gly Gly
465                 470                 475                 480

Leu Ser Ile Ala Val Glu Gly Pro Ser Lys Ala Glu Ile Thr Phe Asp
            485                 490                 495

Asp His Lys Asn Gly Ser Cys Gly Val Ser Tyr Ile Ala Gln Glu Pro
            500                 505                 510

Gly Asn Tyr Glu Val Ser Ile Lys Phe Asn Asp Glu His Ile Pro Glu
            515                 520                 525

Ser Pro Tyr Leu Val Pro Val Ile Ala Pro Ser Asp Asp Ala Arg Arg
            530                 535                 540

Leu Thr Val Met Ser Leu Gln Glu Ser Gly Leu Lys Val Asn Gln Pro
545                 550                 555                 560

Ala Ser Phe Ala Ile Arg Leu Asn Gly Ala Lys Gly Lys Ile Asp Ala
            565                 570                 575

Lys Val His Ser Pro Ser Gly Ala Val Glu Glu Cys His Val Ser Glu
            580                 585                 590

Leu Glu Pro Asp Lys Tyr Ala Val Arg Phe Ile Pro His Glu Asn Gly
```

```
                    595                 600                 605
Val His Thr Ile Asp Val Lys Phe Asn Gly Ser His Val Val Gly Ser
            610                 615                 620

Pro Phe Lys Val Arg Val Gly Glu Pro Gly Gln Ala Gly Asn Pro Ala
625                 630                 635                 640

Leu Val Ser Ala Tyr Gly Thr Gly Leu Glu Gly Xaa Thr Thr Gly Ile
                645                 650                 655

Gln Ser Glu Phe Phe Ile Asn Thr Thr Arg Ala Gly Pro Gly Thr Leu
            660                 665                 670

Ser Val Thr Ile Glu Gly Pro Ser Lys Val Lys Met Asp Cys Gln Glu
            675                 680                 685

Thr Pro Glu Gly Tyr Lys Val Met Tyr Thr Pro Met Ala Pro Gly Asn
            690                 695                 700

Tyr Leu Ile Ser Val Lys Tyr Gly Pro Asn His Ile Val Gly Ser
705                 710                 715                 720

Pro Phe Lys Ala Lys Val Thr Gly Gln Arg Leu Val Ser Pro Gly Ser
                725                 730                 735

Ala Asn Glu Thr Ser Ser Ile Leu Val Glu Ser Val Thr Arg Ser Ser
            740                 745                 750

Thr Glu Thr Cys Tyr Ser Ala Ile Pro Lys Ala Ser Ser Asp Ala Ser
            755                 760                 765

Lys Val Thr Ser Lys Gly Ala Gly Leu Ser Lys Ala Phe Val Gly Gln
            770                 775                 780

Lys Ser Ser Phe Leu Val Asp Cys Ser Lys Ala Gly Ser Asn Met Leu
785                 790                 795                 800

Leu Ile Gly Val His Gly Pro Thr Thr Pro Cys Glu Glu Val Ser Met
                805                 810                 815

Lys His Val Gly Asn Gln Gln Tyr Asn Val Thr Tyr Val Val Lys Glu
            820                 825                 830

Arg Gly Asp Tyr Val Leu Ala Val Lys Trp Gly Glu Glu His Ile Pro
            835                 840                 845

Gly Ser Pro Phe His Val Thr Val Pro Tyr
850                 855
```

(2) INFORMATION FOR SEQ ID NO:3:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

CGGATCCTCG GATACCGGCT CTCGGTGAAG                          30

(2) INFORMATION FOR SEQ ID NO:4:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

CGGCTCCTCA GAGAGTGGGA CTGTCTGCCT                          30

(2) INFORMATION FOR SEQ ID NO:5:

(i) SEQUENCE CHARACTERISTICS:
        (A) LENGTH: 545 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..534

(xi) SEQUENCE DESCRIPTION: SEQ ID NO:5:

```
AAG GTG AAG ATG GAT TGC CAG GAG TGC CCT GAG GGC TAC CGC GTC ACC        48
Lys Val Lys Met Asp Cys Gln Glu Cys Pro Glu Gly Tyr Arg Val Thr
 1               5                  10                  15

TAT ACC CCC ATG GCA CCT GGC AGC TAC CTC ATC TCC ATC AAG TAC GGC        96
Tyr Thr Pro Met Ala Pro Gly Ser Tyr Leu Ile Ser Ile Lys Tyr Gly
             20                  25                  30

GGC CCC TAC CAC ATT GGG GGC AGC CCC TTC AAG GCC AAA GTC ACA GGC       144
Gly Pro Tyr His Ile Gly Gly Ser Pro Phe Lys Ala Lys Val Thr Gly
         35                  40                  45

CCC CGT CTC GTC AGC AAC CAC AGC CTC CAC GAG ACA TCA TCA GTG TTT       192
Pro Arg Leu Val Ser Asn His Ser Leu His Glu Thr Ser Ser Val Phe
     50                  55                  60

GTA GAC TCT CTG ACC AAG GCC ACC TGT GCC CCC CAG CAT GGG GCC CCG       240
Val Asp Ser Leu Thr Lys Ala Thr Cys Ala Pro Gln His Gly Ala Pro
 65                  70                  75                  80

GGT CCT GGG CCT GCT GAC GCC AGC AAG GTG GTG GCC AAG GGC CTG GGG       288
Gly Pro Gly Pro Ala Asp Ala Ser Lys Val Val Ala Lys Gly Leu Gly
                 85                  90                  95

CTG AGC AAG GCC TAC GTA GGC CAG AAG AGC AGC TTC ACA GTA GAC TGC       336
Leu Ser Lys Ala Tyr Val Gly Gln Lys Ser Ser Phe Thr Val Asp Cys
             100                 105                 110

AGC AAA GCA GGC AAC AAC ATG CTG CTG GTG GGG GTT CAT GGC CCA AGG       384
Ser Lys Ala Gly Asn Asn Met Leu Leu Val Gly Val His Gly Pro Arg
         115                 120                 125

ACC CCC TGC GAG GAG ATC CTG GTG AAG CAC GTG GGC AGC CGG CTC TAC       432
Thr Pro Cys Glu Glu Ile Leu Val Lys His Val Gly Ser Arg Leu Tyr
     130                 135                 140

AGC GTG TCC TAC CTG CTC AAG GAC AAG GGG GAG TAC ACA CTG GTG GTC       480
Ser Val Ser Tyr Leu Leu Lys Asp Lys Gly Glu Tyr Thr Leu Val Val
145                 150                 155                 160

AAA TGG GGG GAC GAG CAC ATC CCA GGC AGN CCC TAC CGN GTT GTG GTG       528
Lys Trp Gly Asp Glu His Ile Pro Gly Xaa Pro Tyr Xaa Val Val Val
                 165                 170                 175

CCC TGAGTCTTGG GGCC                                                    545
Pro
```

(2) INFORMATION FOR SEQ ID NO:6:

(i) SEQUENCE CHARACTERISTICS:
        (A) LENGTH: 177 amino acids
        (B) TYPE: amino acid
        (D) TOPOLOGY: linear (ii) MOLECULE TYPE: protein (xi) SEQUENCE DESCRIPTION: SEQ ID NO:6:

```
Lys Val Lys Met Asp Cys Gln Glu Cys Pro Glu Gly Tyr Arg Val Thr
 1               5                  10                  15

Tyr Thr Pro Met Ala Pro Gly Ser Tyr Leu Ile Ser Ile Lys Tyr Gly
```

```
                20                   25                     30
Gly Pro Tyr His Ile Gly Gly Ser Pro Phe Lys Ala Lys Val Thr Gly
            35                   40                   45

Pro Arg Leu Val Ser Asn His Ser Leu His Glu Thr Ser Ser Val Phe
        50                  55                   60

Val Asp Ser Leu Thr Lys Ala Thr Cys Ala Pro Gln His Gly Ala Pro
65                   70                   75                   80

Gly Pro Gly Pro Ala Asp Ala Ser Lys Val Val Ala Lys Gly Leu Gly
                85                   90                   95

Leu Ser Lys Ala Tyr Val Gly Gln Lys Ser Ser Phe Thr Val Asp Cys
            100                  105                  110

Ser Lys Ala Gly Asn Asn Met Leu Leu Val Gly Val His Gly Pro Arg
        115                  120                  125

Thr Pro Cys Glu Glu Ile Leu Val Lys His Val Gly Ser Arg Leu Tyr
    130                  135                  140

Ser Val Ser Tyr Leu Leu Lys Asp Lys Gly Glu Tyr Thr Leu Val Val
145                  150                  155                  160

Lys Trp Gly Asp Glu His Ile Pro Gly Xaa Pro Tyr Xaa Val Val Val
                165                  170                  175

Pro (2) INFORMATION FOR SEQ ID NO:7:

(i) SEQUENCE CHARACTERISTICS:
         (A) LENGTH: 8367 base pairs
         (B) TYPE: nucleic acid
         (C) STRANDEDNESS: single
         (D) TOPOLOGY: linear (ii) MOLECULE TYPE: cDNA (ix) FEATURE:
         (A) NAME/KEY: CDS
         (B) LOCATION: 172..8115

(xi) SEQUENCE DESCRIPTION: SEQ ID NO:7:

CGATCCGGGC GCCACCCCGC GGTCATCGGT CACCGGTCGC TCTCAGGAAC AGCAGCGCAA       60

CCTCTGCTCC CTGCCTCGCC TCCCGCGCGC CTAGGTGCCT GCGACTTTAA TTAAAGGGCC      120

GTCCCCTCGC CGAGGCTGCA GCACCGCCCC CCCGGCTTCT CGCGCCTCAA A ATG AGT       177
                                                          Met Ser
                                                          1

AGC TCC CAC TCT CGG GCG GGC CAG AGC GCA GCA GGC GCG GCT CCG GGC        225
Ser Ser His Ser Arg Ala Gly Gln Ser Ala Ala Gly Ala Ala Pro Gly
        5                   10                  15

GGC GGC GTC GAC ACG CGG GAC GCC GAG ATG CCG GCC ACC GAG AAG GAC        273
Gly Gly Val Asp Thr Arg Asp Ala Glu Met Pro Ala Thr Glu Lys Asp
    20                  25                  30

CTG GCG GAG GAC GCG CCG TGG AAG AAG ATC CAG CAG AAC ACT TTC ACG        321
Leu Ala Glu Asp Ala Pro Trp Lys Lys Ile Gln Gln Asn Thr Phe Thr
35                  40                  45                  50

CGC TGG TGC AAC GAG CAC CTG AAG TGC GTG AGC AAG CGC ATC GCC AAC        369
Arg Trp Cys Asn Glu His Leu Lys Cys Val Ser Lys Arg Ile Ala Asn
                55                  60                  65

CTG CAG ACG GAC CTG AGC GAC GGG CTG CGG CTT ATC GCG CTG TTG GAG        417
Leu Gln Thr Asp Leu Ser Asp Gly Leu Arg Leu Ile Ala Leu Leu Glu
            70                  75                  80

GTG CTC AGC CAG AAG AAG ATG CAC CGC AAG CAC AAC CAG CGG CCC ACT        465
Val Leu Ser Gln Lys Lys Met His Arg Lys His Asn Gln Arg Pro Thr
        85                  90                  95
```

-continued

| | | |
|---|---|---|
| TTC CGC CAA ATG CAG CTT GAG AAC GTG TCG GTG GCG CTC GAG TTC CTG<br>Phe Arg Gln Met Gln Leu Glu Asn Val Ser Val Ala Leu Glu Phe Leu<br>100                         105                      110 | 513 |
| GAC CGC GAG AGC ATC AAA CTG GTG TCC ATC GAC AGC AAG GCC ATC GTG<br>Asp Arg Glu Ser Ile Lys Leu Val Ser Ile Asp Ser Lys Ala Ile Val<br>115                       120                      125                   130 | 561 |
| GAC GGG AAC CTG AAG CTG ATC CTG GGC CTC ATC TGG ACC CTG ATC CTG<br>Asp Gly Asn Leu Lys Leu Ile Leu Gly Leu Ile Trp Thr Leu Ile Leu<br>                      135                       140                       145 | 609 |
| CAC TAC TCC ATC TCC ATG CCC ATG TGG GAC GAG GAG GAG GAT GAG GAG<br>His Tyr Ser Ile Ser Met Pro Met Trp Asp Glu Glu Glu Asp Glu Glu<br>                   150                       155                       160 | 657 |
| GCC AAG AAG CAG ACC CCC AAG CAG AGG CTC CTG GGC TGG ATC CAG AAC<br>Ala Lys Lys Gln Thr Pro Lys Gln Arg Leu Leu Gly Trp Ile Gln Asn<br>165                       170                      175 | 705 |
| AAG CTG CCG CAG CTG CCC ATC ACC AAC TTC AGC CGG GAC TGG CAG AGC<br>Lys Leu Pro Gln Leu Pro Ile Thr Asn Phe Ser Arg Asp Trp Gln Ser<br>    180                       185                       190 | 753 |
| GGC CGG GCC CTG GGC GCC CTG GTG GAC AGC TGT GCC CCG GGC CTG TGT<br>Gly Arg Ala Leu Gly Ala Leu Val Asp Ser Cys Ala Pro Gly Leu Cys<br>195                       200                      205                   210 | 801 |
| CCT GAC TGG GAC TCT TGG GAC GCC AGC AAG CCC GTT ACC AAT GCG CGA<br>Pro Asp Trp Asp Ser Trp Asp Ala Ser Lys Pro Val Thr Asn Ala Arg<br>                   215                       220                       225 | 849 |
| GAG GCC ATG CAG CAG GCG GAT GAC TGG CTG GGC ATC CCC CAG GTG ATC<br>Glu Ala Met Gln Gln Ala Asp Asp Trp Leu Gly Ile Pro Gln Val Ile<br>                   230                       235                       240 | 897 |
| ACC CCC GAG GAG ATT GTG GAC CCC AAC GTG GAC GAG CAC TCT GTC ATG<br>Thr Pro Glu Glu Ile Val Asp Pro Asn Val Asp Glu His Ser Val Met<br>                 245                       250                       255 | 945 |
| ACC TAC CTG TCC CAG TTC CCC AAG GCC AAG CTG AAG CCA GGG GCT CCC<br>Thr Tyr Leu Ser Gln Phe Pro Lys Ala Lys Leu Lys Pro Gly Ala Pro<br>260                       265                      270 | 993 |
| TTG CGC CCC AAA CTG AAC CCG AAG AAA GCC CGT GCC TAC GGG CCA GGC<br>Leu Arg Pro Lys Leu Asn Pro Lys Lys Ala Arg Ala Tyr Gly Pro Gly<br>275                       280                      285                   290 | 1041 |
| ATC GAG CCC ACA GGC AAC ATG GTG AAG AAG CGG GCA GAG TTC ACT GTG<br>Ile Glu Pro Thr Gly Asn Met Val Lys Lys Arg Ala Glu Phe Thr Val<br>                   295                       300                       305 | 1089 |
| GAG ACC AGA AGT GCT GGC CAG GGA GAG GTG CTG GTG TAC GTG GAG GAC<br>Glu Thr Arg Ser Ala Gly Gln Gly Glu Val Leu Val Tyr Val Glu Asp<br>                   310                       315                       320 | 1137 |
| CCG GCC GGA CAC CAG GAG GAG GCA AAA GTG ACC GCC AAT AAC GAC AAG<br>Pro Ala Gly His Gln Glu Glu Ala Lys Val Thr Ala Asn Asn Asp Lys<br>325                       330                      335 | 1185 |
| AAC CGC ACC TTC TCC GTC TGG TAC GTC CCC GAG GTG ACG GGG ACT CAT<br>Asn Arg Thr Phe Ser Val Trp Tyr Val Pro Glu Val Thr Gly Thr His<br>    340                       345                       350 | 1233 |
| AAG GTT ACT GTG CTC TTT GCT GGC CAG CAC ATC GCC AAG AGC CCC TTC<br>Lys Val Thr Val Leu Phe Ala Gly Gln His Ile Ala Lys Ser Pro Phe<br>355                       360                      365                   370 | 1281 |
| GAG GTG TAC GTG GAT AAG TCA CAG GGT GAC GCC AGC AAA GTG ACA GCC<br>Glu Val Tyr Val Asp Lys Ser Gln Gly Asp Ala Ser Lys Val Thr Ala<br>                   375                       380                       385 | 1329 |
| CAA GGT CCC GGC CTG GAG CCC AGT GGC AAC ATC GCC AAC AAG ACC ACC<br>Gln Gly Pro Gly Leu Glu Pro Ser Gly Asn Ile Ala Asn Lys Thr Thr<br>                   390                       395                       400 | 1377 |
| TAC TTT GAG ATC TTT ACG GCA GGA GCT GGC ACG GGC GAG GTC GAG GTT<br>Tyr Phe Glu Ile Phe Thr Ala Gly Ala Gly Thr Gly Glu Val Glu Val<br>                   405                       410                       415 | 1425 |

```
GTG ATC CAG GAC CCC ATG GGA CAG AAG GGC ACG GTA GAG CCT CAG CTG    1473
Val Ile Gln Asp Pro Met Gly Gln Lys Gly Thr Val Glu Pro Gln Leu
    420                 425                 430

GAG GCC CGG GGC GAC AGC ACA TAC CGC TGC AGC TAC CAG CCC ACC ATG    1521
Glu Ala Arg Gly Asp Ser Thr Tyr Arg Cys Ser Tyr Gln Pro Thr Met
435                 440                 445                 450

GAG GGC GTC CAC ACC GTG CAC GTC ACG TTT GCC GGC GTG CCC ATC CCT    1569
Glu Gly Val His Thr Val His Val Thr Phe Ala Gly Val Pro Ile Pro
                455                 460                 465

CGC AGC CCC TAC ACT GTC ACT GTT GGC CAA GCC TGT AAC CCG AGT GCC    1617
Arg Ser Pro Tyr Thr Val Thr Val Gly Gln Ala Cys Asn Pro Ser Ala
            470                 475                 480

TGC CGG GCG GTT GGC CGG GGC CTC CAG CCC AAG GGT GTG CGG GTG AAG    1665
Cys Arg Ala Val Gly Arg Gly Leu Gln Pro Lys Gly Val Arg Val Lys
        485                 490                 495

GAG ACA GCT GAC TTC AAG GTG TAC ACA AAG GGC GCT GGC AGT GGG GAG    1713
Glu Thr Ala Asp Phe Lys Val Tyr Thr Lys Gly Ala Gly Ser Gly Glu
500                 505                 510

CTG AAG GTC ACC GTG AAG GGC CCC AAG GGA GAG GAG CGC GTG AAG CAG    1761
Leu Lys Val Thr Val Lys Gly Pro Lys Gly Glu Glu Arg Val Lys Gln
515                 520                 525                 530

AAG GAC CTG GGG GAT GGC GTG TAT GGC TTC GAG TAT TAC CCC ATG GTC    1809
Lys Asp Leu Gly Asp Gly Val Tyr Gly Phe Glu Tyr Tyr Pro Met Val
                535                 540                 545

CCT GGA ACC TAT ATC GTC ACC ATC ACG TGG GGT GGT CAG AAC ATC GGG    1857
Pro Gly Thr Tyr Ile Val Thr Ile Thr Trp Gly Gly Gln Asn Ile Gly
            550                 555                 560

CGC AGT CCC TTC GAA GTG AAG GTG GGC ACC GAG TGT GGC AAT CAG AAG    1905
Arg Ser Pro Phe Glu Val Lys Val Gly Thr Glu Cys Gly Asn Gln Lys
        565                 570                 575

GTA CGG GCC TGG GGC CCT GGG CTG GAG GGC GGC GTC GTT GGC AAG TCA    1953
Val Arg Ala Trp Gly Pro Gly Leu Glu Gly Gly Val Val Gly Lys Ser
580                 585                 590

GCA GAC TTT GTG GTG GAG GCT ATC GGG GAC GAC GTG GGC ACG CTG GGC    2001
Ala Asp Phe Val Val Glu Ala Ile Gly Asp Asp Val Gly Thr Leu Gly
595                 600                 605                 610

TTC TCG GTG GAA GGG CCA TCG CAG GCT AAG ATC GAA TGT GAC GAC AAG    2049
Phe Ser Val Glu Gly Pro Ser Gln Ala Lys Ile Glu Cys Asp Asp Lys
                615                 620                 625

GGC GAC GGC TCC TGT GAT GTG CGC TAC TGG CCG CAG GAG GCT GGC GAG    2097
Gly Asp Gly Ser Cys Asp Val Arg Tyr Trp Pro Gln Glu Ala Gly Glu
            630                 635                 640

TAT GCC GTT CAC GTG CTG TGC AAC AGC GAA GAC ATC CGC CTC AGC CCC    2145
Tyr Ala Val His Val Leu Cys Asn Ser Glu Asp Ile Arg Leu Ser Pro
        645                 650                 655

TTC ATG GCT GAC ATC CGT GAC GCG CCC CAG GAC TTC CAC CCA GAC AGG    2193
Phe Met Ala Asp Ile Arg Asp Ala Pro Gln Asp Phe His Pro Asp Arg
660                 665                 670

GTG AAG GCA CGT GGG CCT GGA TTG GAG AAG ACA GGT GTG GCC GTC AAC    2241
Val Lys Ala Arg Gly Pro Gly Leu Glu Lys Thr Gly Val Ala Val Asn
675                 680                 685                 690

AAG CCA GCA GAG TTC ACA GTG GAT GCC AAG CAC GGT GGC AAG GCC CCA    2289
Lys Pro Ala Glu Phe Thr Val Asp Ala Lys His Gly Gly Lys Ala Pro
                695                 700                 705

CTT CGG GTC CAA GTC CAG GAC AAT GAA GGC TGC CCT GTG GAG GCG TTG    2337
Leu Arg Val Gln Val Gln Asp Asn Glu Gly Cys Pro Val Glu Ala Leu
            710                 715                 720

GTC AAG GAC AAC GGC AAT GGC ACT TAC AGC TGC TCC TAC GTG CCC AGG    2385
Val Lys Asp Asn Gly Asn Gly Thr Tyr Ser Cys Ser Tyr Val Pro Arg
        725                 730                 735
```

| | |
|---|---|
| AAG CCG GTG AAG CAC ACA GCC ATG GTG TCC TGG GGA GGC GTC AGC ATC<br>Lys Pro Val Lys His Thr Ala Met Val Ser Trp Gly Gly Val Ser Ile<br>740                              745                      750 | 2433 |
| CCC AAC AGC CCC TTC AGG GTG AAT GTG GGA GCT GGC AGC CAC CCC AAC<br>Pro Asn Ser Pro Phe Arg Val Asn Val Gly Ala Gly Ser His Pro Asn<br>755                      760                      765                      770 | 2481 |
| AAG GTC AAA GTA TAC GGC CCC GGA GTA GCC AAG ACA GGG CTC AAG GCC<br>Lys Val Lys Val Tyr Gly Pro Gly Val Ala Lys Thr Gly Leu Lys Ala<br>                      775                      780                      785 | 2529 |
| CAC GAG CCC ACC TAC TTC ACT GTG GAC TGC GCC GAG GCT GGC CAG GGG<br>His Glu Pro Thr Tyr Phe Thr Val Asp Cys Ala Glu Ala Gly Gln Gly<br>                  790                      795                      800 | 2577 |
| GAC GTC AGC ATC GGC ATC AAG TGT GCC CCT GGA GTG GTA GGC CCC GCC<br>Asp Val Ser Ile Gly Ile Lys Cys Ala Pro Gly Val Val Gly Pro Ala<br>805                              810                      815 | 2625 |
| GAA GCT GAC ATC GAC TTC GAC ATC ATC CGC AAT GAC AAT GAC ACC TTC<br>Glu Ala Asp Ile Asp Phe Asp Ile Ile Arg Asn Asp Asn Asp Thr Phe<br>820                              825                      830 | 2673 |
| ACG GTC AAG TAC ACG CCC CGG GGG GCT GGC AGC TAC ACC ATT ATG GTC<br>Thr Val Lys Tyr Thr Pro Arg Gly Ala Gly Ser Tyr Thr Ile Met Val<br>835                      840                      845                      850 | 2721 |
| CTC TTT GCT GAC CAG GCC ACG CCC ACC AGC CCC ATC CGA GTC AAG GTG<br>Leu Phe Ala Asp Gln Ala Thr Pro Thr Ser Pro Ile Arg Val Lys Val<br>                  855                      860                      865 | 2769 |
| GAG CCC TCT CAT GAC GCC AGT AAG GTG AAG GCC GAG GGC CCT GGC CTC<br>Glu Pro Ser His Asp Ala Ser Lys Val Lys Ala Glu Gly Pro Gly Leu<br>                  870                      875                      880 | 2817 |
| AGT CGC ACT GGT GTC GAG CTT GGC AAG CCC ACC CAC TTC ACA GTA AAT<br>Ser Arg Thr Gly Val Glu Leu Gly Lys Pro Thr His Phe Thr Val Asn<br>                  885                      890                      895 | 2865 |
| GCC AAA GCT GCT GGC AAA GGC AAG CTG GAC GTC CAG TTC TCA GGA CTC<br>Ala Lys Ala Ala Gly Lys Gly Lys Leu Asp Val Gln Phe Ser Gly Leu<br>900                              905                      910 | 2913 |
| ACC AAG GGG GAT GCA GTG CGA GAT GTG GAC ATC ATC GAC CAC CAT GAC<br>Thr Lys Gly Asp Ala Val Arg Asp Val Asp Ile Ile Asp His His Asp<br>915                              920                      925                      930 | 2961 |
| AAC ACC TAC ACA GTC AAG TAC ACG CCT GTC CAG CAG GGT CCA GTA GGC<br>Asn Thr Tyr Thr Val Lys Tyr Thr Pro Val Gln Gln Gly Pro Val Gly<br>                  935                      940                      945 | 3009 |
| GTC AAT GTC ACT TAT GGA GGG GAT CCC ATC CCT AAG AGC CCT TTC TCA<br>Val Asn Val Thr Tyr Gly Gly Asp Pro Ile Pro Lys Ser Pro Phe Ser<br>950                              955                      960 | 3057 |
| GTG GCA GTA TCT CCA AGC CTG GAC CTC AGC AAG ATC AAG GTG TCT GGC<br>Val Ala Val Ser Pro Ser Leu Asp Leu Ser Lys Ile Lys Val Ser Gly<br>                  965                      970                      975 | 3105 |
| CTG GGA GAG AAG GTG GAC GTT GGC AAA GAC CAG GAG TTC ACA GTC AAA<br>Leu Gly Glu Lys Val Asp Val Gly Lys Asp Gln Glu Phe Thr Val Lys<br>980                              985                      990 | 3153 |
| TCA AAG GGT GCT GGT GGT CAA GGC AAA GTG GCA TCC AAG ATT GTG GGC<br>Ser Lys Gly Ala Gly Gly Gln Gly Lys Val Ala Ser Lys Ile Val Gly<br>995                        1000                   1005                   1010 | 3201 |
| CCC TCG GGT GCA GCG GTG CCC TGC AAG GTG GAG CCA GGC CTG GGG GCT<br>Pro Ser Gly Ala Ala Val Pro Cys Lys Val Glu Pro Gly Leu Gly Ala<br>                  1015                   1020                   1025 | 3249 |
| GAC AAC AGT GTG GTG CGC TTC CTG CCC CGT GAG GAA GGG CCC TAT GAG<br>Asp Asn Ser Val Val Arg Phe Leu Pro Arg Glu Glu Gly Pro Tyr Glu<br>                  1030                   1035                   1040 | 3297 |
| GTG GAG GTG ACC TAT GAC GGC GTG CCC GTG CCT GGC AGC CCC TTT CCT<br>Val Glu Val Thr Tyr Asp Gly Val Pro Val Pro Gly Ser Pro Phe Pro<br>1045                             1050                   1055 | 3345 |

-continued

| | |
|---|---|
| CTG GAA GCT GTG GCC CCC ACC AAG CCT AGC AAG GTG AAG GCG TTT GGG<br>Leu Glu Ala Val Ala Pro Thr Lys Pro Ser Lys Val Lys Ala Phe Gly<br>1060                    1065                    1070 | 3393 |
| CCG GGG CTG CAG GGA GGC AGT GCG GGC TCC CCC GCC CGC TTC ACC ATC<br>Pro Gly Leu Gln Gly Gly Ser Ala Gly Ser Pro Ala Arg Phe Thr Ile<br>1075                   1080                 1085                 1090 | 3441 |
| GAC ACC AAG GGC GCC GGC ACA GGT GGC CTG GGC CTG ACG GTG GAG GGC<br>Asp Thr Lys Gly Ala Gly Thr Gly Gly Leu Gly Leu Thr Val Glu Gly<br>                  1095                 1100                 1105 | 3489 |
| CCC TGT GAG GCG CAG CTC GAG TGC TTG GAC AAT GGG GAT GGC ACA TGT<br>Pro Cys Glu Ala Gln Leu Glu Cys Leu Asp Asn Gly Asp Gly Thr Cys<br>1110                    1115                    1120 | 3537 |
| TCC GTG TCC TAC GTG CCC ACC GAG CCC GGG GAC TAC AAC ATC AAC ATC<br>Ser Val Ser Tyr Val Pro Thr Glu Pro Gly Asp Tyr Asn Ile Asn Ile<br>                  1125                 1130                 1135 | 3585 |
| CTC TTC GCT GAC ACC CAC ATC CCT GGC TCC CCA TTC AAG GCC CAC GTG<br>Leu Phe Ala Asp Thr His Ile Pro Gly Ser Pro Phe Lys Ala His Val<br>1140                    1145                    1150 | 3633 |
| GTT CCC TGC TTT GAC GCA TCC AAA GTC AAG TGC TCA GGC CCC GGG CTG<br>Val Pro Cys Phe Asp Ala Ser Lys Val Lys Cys Ser Gly Pro Gly Leu<br>1155                    1160                    1165                    1170 | 3681 |
| GAG CGG GCC ACC GCT GGG GAG GTG GGC CAA TTC CAA GTG GAC TGC TCG<br>Glu Arg Ala Thr Ala Gly Glu Val Gly Gln Phe Gln Val Asp Cys Ser<br>                  1175                 1180                 1185 | 3729 |
| AGC GCG GGC AGC GCG GAG CTG ACC ATT GAG ATC TGC TCG GAG GCG GGG<br>Ser Ala Gly Ser Ala Glu Leu Thr Ile Glu Ile Cys Ser Glu Ala Gly<br>                  1190                 1195                 1200 | 3777 |
| CTT CCG GCC GAG GTG TAC ATC CAG GAC CAC GGT GAT GGC ACG CAC ACC<br>Leu Pro Ala Glu Val Tyr Ile Gln Asp His Gly Asp Gly Thr His Thr<br>                  1205                 1210                 1215 | 3825 |
| ATT ACC TAC ATT CCC CTC TGC CCC GGG GCC TAC ACC GTC ACC ATC AAG<br>Ile Thr Tyr Ile Pro Leu Cys Pro Gly Ala Tyr Thr Val Thr Ile Lys<br>                  1220                 1225                 1230 | 3873 |
| TAC GGC GGC CAG CCC GTG CCC AAC TTC CCC AGC AAG CTG CAG GTG GAA<br>Tyr Gly Gly Gln Pro Val Pro Asn Phe Pro Ser Lys Leu Gln Val Glu<br>1235                    1240                    1245                    1250 | 3921 |
| CCT GCG GTG GAC ACT TCC GGT GTC CAG TGC TAT GGG CCT GGT ATT GAG<br>Pro Ala Val Asp Thr Ser Gly Val Gln Cys Tyr Gly Pro Gly Ile Glu<br>                  1255                 1260                 1265 | 3969 |
| GGC CAG GGT GTC TTC CGT GAG GCC ACC ACT GAG TTC AGT GTG GAC GCC<br>Gly Gln Gly Val Phe Arg Glu Ala Thr Thr Glu Phe Ser Val Asp Ala<br>                  1270                 1275                 1280 | 4017 |
| CGG GCT CTG ACA CAG ACC GGA GGG CCG CAC GTC AAG GCC CGT GTG GCC<br>Arg Ala Leu Thr Gln Thr Gly Gly Pro His Val Lys Ala Arg Val Ala<br>                  1285                 1290                 1295 | 4065 |
| AAC CCC TCA GGC AAC CTG ACG GAG ACC TAC GTT CAG GAC CGT GGC GAT<br>Asn Pro Ser Gly Asn Leu Thr Glu Thr Tyr Val Gln Asp Arg Gly Asp<br>1300                    1305                    1310 | 4113 |
| GGC ATG TAC AAA GTG GAG TAC ACG CCT TAC GAG GAG GGA CTG CAC TCC<br>Gly Met Tyr Lys Val Glu Tyr Thr Pro Tyr Glu Glu Gly Leu His Ser<br>1315                    1320                    1325                    1330 | 4161 |
| GTG GAC GTG ACC TAT GAC GGC AGT CCC GTG CCC AGC AGC CCC TTC CAG<br>Val Asp Val Thr Tyr Asp Gly Ser Pro Val Pro Ser Ser Pro Phe Gln<br>                  1335                 1340                 1345 | 4209 |
| GTG CCC GTG ACC GAG GGC TGC GAC CCC TCC CGG GTG CGT GTC CAC GGG<br>Val Pro Val Thr Glu Gly Cys Asp Pro Ser Arg Val Arg Val His Gly<br>                  1350                 1355                 1360 | 4257 |
| CCA GGC ATC CAA AGT GGC ACC ACC AAC AAG CCC AAC AAG TTC ACT GTG<br>Pro Gly Ile Gln Ser Gly Thr Thr Asn Lys Pro Asn Lys Phe Thr Val<br>1365                    1370                    1375 | 4305 |

-continued

| | |
|---|---|
| GAG ACC AGG GGA GCT GGC ACG GGC GGC CTG GGC CTG GCT GTA GAG GGC<br>Glu Thr Arg Gly Ala Gly Thr Gly Gly Leu Gly Leu Ala Val Glu Gly<br>1380     1385     1390 | 4353 |
| CCC TCC GAG GCC AAG ATG TCC TGC ATG GAT AAC AAG GAC GGC AGC TGC<br>Pro Ser Glu Ala Lys Met Ser Cys Met Asp Asn Lys Asp Gly Ser Cys<br>1395     1400     1405     1410 | 4401 |
| TCG GTC GAG TAC ATC CCT TAT GAG GCT GGC ACC TAC AGC CTC AAC GTC<br>Ser Val Glu Tyr Ile Pro Tyr Glu Ala Gly Thr Tyr Ser Leu Asn Val<br>     1415     1420     1425 | 4449 |
| ACC TAT GGT GGC CAT CAA GTG CCA GGC AGT CCT TTC AAG GTC CCT GTG<br>Thr Tyr Gly Gly His Gln Val Pro Gly Ser Pro Phe Lys Val Pro Val<br>1430     1435     1440 | 4497 |
| CAT GAT GTG ACA GAT GCG TCC AAG GTC AAG TGC TCT GGG CCC GGC CTG<br>His Asp Val Thr Asp Ala Ser Lys Val Lys Cys Ser Gly Pro Gly Leu<br>     1445     1450     1455 | 4545 |
| AGC CCA GGC ATG GTT CGT GCC AAC CTC CCT CAG TCC TTC CAG GTG GAC<br>Ser Pro Gly Met Val Arg Ala Asn Leu Pro Gln Ser Phe Gln Val Asp<br>1460     1465     1470 | 4593 |
| ACA AGC AAG GCT GGT GTG GCC CCA TTG CAG GTC AAA GTG CAA GGG CCC<br>Thr Ser Lys Ala Gly Val Ala Pro Leu Gln Val Lys Val Gln Gly Pro<br>1475     1480     1485     1490 | 4641 |
| AAA GGC CTG GTG GAG CCA GTG GAC GTG GTA GAC AAC GCT GAT GGC ACC<br>Lys Gly Leu Val Glu Pro Val Asp Val Val Asp Asn Ala Asp Gly Thr<br>     1495     1500     1505 | 4689 |
| CAG ACC GTC AAT TAT GTG CCC AGC CGA GAA GGG CCC TAC AGC ATC TCA<br>Gln Thr Val Asn Tyr Val Pro Ser Arg Glu Gly Pro Tyr Ser Ile Ser<br>1510     1515     1520 | 4737 |
| GTA CTG TAT GGA GAT GAA GAG GTA CCC CGG AGC CCC TTC AAG GTC AAG<br>Val Leu Tyr Gly Asp Glu Glu Val Pro Arg Ser Pro Phe Lys Val Lys<br>     1525     1530     1535 | 4785 |
| GTG CTG CCT ACT CAT GAT GCC AGC AAG GTG AAG GCC AGT GGC CCC GGG<br>Val Leu Pro Thr His Asp Ala Ser Lys Val Lys Ala Ser Gly Pro Gly<br>1540     1545     1550 | 4833 |
| CTC AAC ACC ACT GGC GTG CCT GCC AGC CTG CCC GTG GAG TTC ACC ATC<br>Leu Asn Thr Thr Gly Val Pro Ala Ser Leu Pro Val Glu Phe Thr Ile<br>1555     1560     1565     1570 | 4881 |
| GAT GCA AAG GAC GCC GGG GAG GGC CTG CTG GCT GTC CAG ATC ACG GAT<br>Asp Ala Lys Asp Ala Gly Glu Gly Leu Leu Ala Val Gln Ile Thr Asp<br>     1575     1580     1585 | 4929 |
| CCC GAA GGC AAG CCG AAG AAG ACA CAC ATC CAA GAC AAC CAT GAC GGC<br>Pro Glu Gly Lys Pro Lys Lys Thr His Ile Gln Asp Asn His Asp Gly<br>1590     1595     1600 | 4977 |
| ACG TAT ACA GTG GCC TAC GTG CCA GAC GTG ACA GGT CGC TAC ACC ATC<br>Thr Tyr Thr Val Ala Tyr Val Pro Asp Val Thr Gly Arg Tyr Thr Ile<br>     1605     1610     1615 | 5025 |
| CTC ATC AAG TAC GGT GGT GAC GAG ATC CCC TTC TCC CCG TAC CGC GTG<br>Leu Ile Lys Tyr Gly Gly Asp Glu Ile Pro Phe Ser Pro Tyr Arg Val<br>1620     1625     1630 | 5073 |
| CGT GCC GTG CCC ACC GGG GAC GCC AGC AAG TGC ACT GTC ACA GTG TCA<br>Arg Ala Val Pro Thr Gly Asp Ala Ser Lys Cys Thr Val Thr Val Ser<br>1635     1640     1645     1650 | 5121 |
| ATC GGA GGT CAC GGG CTA GGT GCT GGC ATC GGC CCC ACC ATT CAG ATT<br>Ile Gly Gly His Gly Leu Gly Ala Gly Ile Gly Pro Thr Ile Gln Ile<br>     1655     1660     1665 | 5169 |
| GGG GAG GAG ACG GTG ATC ACT GTG GAC ACT AAG GCG GCA GGC AAA GGC<br>Gly Glu Glu Thr Val Ile Thr Val Asp Thr Lys Ala Ala Gly Lys Gly<br>1670     1675     1680 | 5217 |
| AAA GTG ACG TGC ACC GTG TGC ACG CCT GAT GGC TCA GAG GTG GAT GTG<br>Lys Val Thr Cys Thr Val Cys Thr Pro Asp Gly Ser Glu Val Asp Val<br>     1685     1690     1695 | 5265 |

| | |
|---|---|
| GAC GTG GTG GAG AAT GAG GAC GGC ACT TTC GAC ATC TTC TAC ACG GCC<br>Asp Val Val Glu Asn Glu Asp Gly Thr Phe Asp Ile Phe Tyr Thr Ala<br>1700                             1705                       1710 | 5313 |
| CCC CAG CCG GGC AAA TAC GTC ATC TGT GTG CGC TTT GGT GGA GAG CAC<br>Pro Gln Pro Gly Lys Tyr Val Ile Cys Val Arg Phe Gly Gly Glu His<br>1715                     1720                     1725                     1730 | 5361 |
| GTG CCC AAC AGC CCC TTC CAA GTG ACG GCT CTG GCT GGG GAC CAG CCC<br>Val Pro Asn Ser Pro Phe Gln Val Thr Ala Leu Ala Gly Asp Gln Pro<br>                 1735                     1740                     1745 | 5409 |
| TCG GTG CAG CCC CCT CTA CGG TCT CAG CAG CTG GCC CCA CAG TAC ACC<br>Ser Val Gln Pro Pro Leu Arg Ser Gln Gln Leu Ala Pro Gln Tyr Thr<br>                 1750                     1755                     1760 | 5457 |
| TAC GCC CAG GGC GGC CAG CAG ACT TGG GCC CCG GAG AGG CCC CTG GTG<br>Tyr Ala Gln Gly Gly Gln Gln Thr Trp Ala Pro Glu Arg Pro Leu Val<br>                 1765                     1770                     1775 | 5505 |
| GGT GTC AAT GGG CTG GAT GTG ACC AGC CTG AGG CCC TTT GAC CTT GTC<br>Gly Val Asn Gly Leu Asp Val Thr Ser Leu Arg Pro Phe Asp Leu Val<br>1780                             1785                       1790 | 5553 |
| ATC CCC TTC ACC ATC AAG AAG GGC GAG ATC ACA GGG GAG GTT CGG ATG<br>Ile Pro Phe Thr Ile Lys Lys Gly Glu Ile Thr Gly Glu Val Arg Met<br>1795                             1800                     1805               1810 | 5601 |
| CCC TCA GGC AAG GTG GCG CAG CCC ACC ATC ACT GAC AAC AAA GAC GGC<br>Pro Ser Gly Lys Val Ala Gln Pro Thr Ile Thr Asp Asn Lys Asp Gly<br>                 1815                     1820                     1825 | 5649 |
| ACC GTG ACC GTG CGG TAT GCA CCC AGC GAG GCT GGC CTG CAC GAG ATG<br>Thr Val Thr Val Arg Tyr Ala Pro Ser Glu Ala Gly Leu His Glu Met<br>                 1830                     1835                     1840 | 5697 |
| GAC ATC CGC TAT GAC AAC ATG CAC ATC CCA GGA AGC CCC TTG CAG TTC<br>Asp Ile Arg Tyr Asp Asn Met His Ile Pro Gly Ser Pro Leu Gln Phe<br>                 1845                     1850                     1855 | 5745 |
| TAT GTG GAT TAC GTC AAC TGT GGC CAT GTC ACT GCC TAT GGG CCT GGC<br>Tyr Val Asp Tyr Val Asn Cys Gly His Val Thr Ala Tyr Gly Pro Gly<br>1860                             1865                     1870 | 5793 |
| CTC ACC CAT GGA GTA GTG AAC AAG CCT GCC ACC TTC ACC GTC AAC ACC<br>Leu Thr His Gly Val Val Asn Lys Pro Ala Thr Phe Thr Val Asn Thr<br>1875                             1880                     1885                     1890 | 5841 |
| AAG GAT GCA GGA GAG GGG GGC CTG TCT CTG GCC ATT GAG GGC CCG TCC<br>Lys Asp Ala Gly Glu Gly Gly Leu Ser Leu Ala Ile Glu Gly Pro Ser<br>                 1895                     1900                     1905 | 5889 |
| AAA GCA GAA ATC AGC TGC ACT GAC AAC CAG GAT GGG ACA TGC AGC GTG<br>Lys Ala Glu Ile Ser Cys Thr Asp Asn Gln Asp Gly Thr Cys Ser Val<br>                 1910                     1915                     1920 | 5937 |
| TCC TAC CTG CCT GTG CTG CCG GGG GAC TAC AGC ATT CTA GTC AAG TAC<br>Ser Tyr Leu Pro Val Leu Pro Gly Asp Tyr Ser Ile Leu Val Lys Tyr<br>                 1925                     1930                     1935 | 5985 |
| AAT GAA CAG CAC GTC CCA GGC AGC CCC TTC ACT GCT CGG GTC ACA GGT<br>Asn Glu Gln His Val Pro Gly Ser Pro Phe Thr Ala Arg Val Thr Gly<br>                 1940                     1945                     1950 | 6033 |
| GAC GAC TCC ATG CGT ATG TCC CAC CTA AAG GTC GGC TCT GCT GCC GAC<br>Asp Asp Ser Met Arg Met Ser His Leu Lys Val Gly Ser Ala Ala Asp<br>1955                             1960                     1965                     1970 | 6081 |
| ATC CCC ATC AAC ATC TCA GAG ACG GAT CTC AGC CTG CTG ACG GCC ACT<br>Ile Pro Ile Asn Ile Ser Glu Thr Asp Leu Ser Leu Leu Thr Ala Thr<br>                 1975                     1980                     1985 | 6129 |
| GTG GTC CCG CCC TCG GGC CGG GAG GAG CCC TGT TTG CTG AAG CGG CTG<br>Val Val Pro Pro Ser Gly Arg Glu Glu Pro Cys Leu Leu Lys Arg Leu<br>                 1990                     1995                     2000 | 6177 |
| CGT AAT GGC CAC GTG GGG ATT TCA TTC GTG CCC AAG GAG ACG GGG GAG<br>Arg Asn Gly His Val Gly Ile Ser Phe Val Pro Lys Glu Thr Gly Glu<br>2005                             2010                     2015 | 6225 |

| | | |
|---|---|---|
| CAC CTG GTG CAT GTG AAG AAA AAT GGC CAG CAC GTG GCC AGC AGC CCC<br>His Leu Val His Val Lys Lys Asn Gly Gln His Val Ala Ser Ser Pro<br>            2020                              2025                       2030 | 6273 |
| ATC CCG GTG GTG ATC AGC CAG TCG GAA ATT GGG GAT GCC AGT CGT GTT<br>Ile Pro Val Val Ile Ser Gln Ser Glu Ile Gly Asp Ala Ser Arg Val<br>2035                    2040                    2045                    2050 | 6321 |
| CGG GTC TCT GGT CAG GGC CTT CAC GAA GGC CAC ACC TTT GAG CCT GCA<br>Arg Val Ser Gly Gln Gly Leu His Glu Gly His Thr Phe Glu Pro Ala<br>            2055                            2060                    2065 | 6369 |
| GAG TTT ATC ATT GAT ACC CGC GAT GCA GGC TAT GGT GGG CTC AGC CTG<br>Glu Phe Ile Ile Asp Thr Arg Asp Ala Gly Tyr Gly Gly Leu Ser Leu<br>                2070                    2075                    2080 | 6417 |
| TCC ATT GAG GGC CCC AGC AAG GTG GAC ATC AAC ACA GAG GAC CTG GAG<br>Ser Ile Glu Gly Pro Ser Lys Val Asp Ile Asn Thr Glu Asp Leu Glu<br>2085                    2090                    2095 | 6465 |
| GAC GGG ACG TGC AGG GTC ACC TAC TGC CCC ACA GAG CCA GGC AAC TAC<br>Asp Gly Thr Cys Arg Val Thr Tyr Cys Pro Thr Glu Pro Gly Asn Tyr<br>            2100                            2105                    2110 | 6513 |
| ATC ATC AAC ATC AAG TTT GCC GAC CAG CAC GTG CCT GGC AGC CCC TTC<br>Ile Ile Asn Ile Lys Phe Ala Asp Gln His Val Pro Gly Ser Pro Phe<br>2115                    2120                    2125                    2130 | 6561 |
| TCT GTG AAG GTG ACA GGC GAG GGC CGG GTG AAA GAG AGC ATC ACC CGC<br>Ser Val Lys Val Thr Gly Glu Gly Arg Val Lys Glu Ser Ile Thr Arg<br>                2135                    2140                    2145 | 6609 |
| AGG CGT CGG GCT CCT TCA GTG GCC AAC GTT GGT AGT CAT TGT GAC CTC<br>Arg Arg Arg Ala Pro Ser Val Ala Asn Val Gly Ser His Cys Asp Leu<br>            2150                            2155                    2160 | 6657 |
| AGC CTG AAA ATC CCT GAA ATT AGC ATC CAG GAT ATG ACA GCC CAG GTG<br>Ser Leu Lys Ile Pro Glu Ile Ser Ile Gln Asp Met Thr Ala Gln Val<br>                2165                    2170                    2175 | 6705 |
| ACC AGC CCA TCG GGC AAG ACC CAT GAG GCC GAG ATC GTG GAA GGG GAG<br>Thr Ser Pro Ser Gly Lys Thr His Glu Ala Glu Ile Val Glu Gly Glu<br>2180                    2185                    2190 | 6753 |
| AAC CAC ACC TAC TGC ATC CGC TTT GTT CCC GCT GAG ATG GGC ACA CAC<br>Asn His Thr Tyr Cys Ile Arg Phe Val Pro Ala Glu Met Gly Thr His<br>2195                    2200                    2205                    2210 | 6801 |
| ACA GTC AGC GTC AAG TAC AAG GGC CAG CAC GTG CCT GGG AGC CCC TTC<br>Thr Val Ser Val Lys Tyr Lys Gly Gln His Val Pro Gly Ser Pro Phe<br>                2215                    2220                    2225 | 6849 |
| CAG TTC ACC GTG GGG CCC CTA GGG GAA GGG GGA GCC CAC AAG GTC CGA<br>Gln Phe Thr Val Gly Pro Leu Gly Glu Gly Gly Ala His Lys Val Arg<br>            2230                            2235                    2240 | 6897 |
| GCT GGG GGC CCT GGC CTG GAG AGA GCT GAA GCT GGA GTG CCA GCC GAA<br>Ala Gly Gly Pro Gly Leu Glu Arg Ala Glu Ala Gly Val Pro Ala Glu<br>                2245                    2250                    2255 | 6945 |
| TTC AGT ATC TGG ACC CGG GAA GCT GGT GCT GGA GGC CTG GCC ATT GCT<br>Phe Ser Ile Trp Thr Arg Glu Ala Gly Ala Gly Gly Leu Ala Ile Ala<br>            2260                            2265                    2270 | 6993 |
| GTC GAG GGC CCC AGC AAG GCT GAG ATC TCT TTT GAG GAC CGC AAG GAC<br>Val Glu Gly Pro Ser Lys Ala Glu Ile Ser Phe Glu Asp Arg Lys Asp<br>2275                    2280                    2285                    2290 | 7041 |
| GGC TCC TGT GGT GTG GCT TAT GTG GTC CAG GAG CCA GGT GAC TAC GAA<br>Gly Ser Cys Gly Val Ala Tyr Val Val Gln Glu Pro Gly Asp Tyr Glu<br>                2295                    2300                    2305 | 7089 |
| GTC TCA GTC AAG TTC AAC GAG GAA CAC ATT CCC GAC AGC CCC TTC GTG<br>Val Ser Val Lys Phe Asn Glu Glu His Ile Pro Asp Ser Pro Phe Val<br>            2310                            2315                    2320 | 7137 |
| GTG CCT GTG GCT TCT CCG TCT GGC GAC GCC CGC CGC CTC ACT GTT TCT<br>Val Pro Val Ala Ser Pro Ser Gly Asp Ala Arg Arg Leu Thr Val Ser<br>                2325                    2330                    2335 | 7185 |

| | | |
|---|---|---|
| AGC CTT CAG GAG TCA GGG CTA AAG GTC AAC CAG CCA GCC TCT TTT GCA<br>Ser Leu Gln Glu Ser Gly Leu Lys Val Asn Gln Pro Ala Ser Phe Ala<br>        2340                       2345                   2350 | 7233 | |
| GTC AGC CTG AAC GGG GCC AAG GGG GCG ATC GAT GCC AAG GTG CAC AGC<br>Val Ser Leu Asn Gly Ala Lys Gly Ala Ile Asp Ala Lys Val His Ser<br>2355                   2360                   2365                   2370 | 7281 | |
| CCC TCA GGA GCC CTG GAG GAG TGC TAT GTC ACA GAA ATT GAC CAA GAT<br>Pro Ser Gly Ala Leu Glu Glu Cys Tyr Val Thr Glu Ile Asp Gln Asp<br>        2375                       2380                   2385 | 7329 | |
| AAG TAT GCT GTG CGC TTC ATC CCT CGG GAG AAT GGC GTT TAC CTG ATT<br>Lys Tyr Ala Val Arg Phe Ile Pro Arg Glu Asn Gly Val Tyr Leu Ile<br>               2390                   2395                   2400 | 7377 | |
| GAC GTC AAG TTC AAC GGT ACC CAC ATC CCT GGA AGC CCC TTC AAG ATC<br>Asp Val Lys Phe Asn Gly Thr His Ile Pro Gly Ser Pro Phe Lys Ile<br>        2405                       2410                   2415 | 7425 | |
| CGA GTT GGG GAG CCT GGG CAT GGA GGG GAC CCA GGC TTG GTG TCT GCT<br>Arg Val Gly Glu Pro Gly His Gly Gly Asp Pro Gly Leu Val Ser Ala<br>2420                   2425                   2430 | 7473 | |
| TAC GGA GCA GGT CTG GAA GGC GGT GTC ACA GGG AAC CCA GCT GAG TTC<br>Tyr Gly Ala Gly Leu Glu Gly Gly Val Thr Gly Asn Pro Ala Glu Phe<br>2435                   2440                   2445                   2450 | 7521 | |
| GTC GTG AAC ACG AGC AAT GCG GGA GCT GGT GCC CTG TCG GTG ACC ATT<br>Val Val Asn Thr Ser Asn Ala Gly Ala Gly Ala Leu Ser Val Thr Ile<br>               2455                   2460                   2465 | 7569 | |
| GAC GGC CCC TCC AAG GTG AAG ATG GAT TGC CAG GAG TGC CCT GAG GGC<br>Asp Gly Pro Ser Lys Val Lys Met Asp Cys Gln Glu Cys Pro Glu Gly<br>        2470                       2475                   2480 | 7617 | |
| TAC CGC GTC ACC TAT ACC CCC ATG GCA CCT GGC AGC TAC CTC ATC TCC<br>Tyr Arg Val Thr Tyr Thr Pro Met Ala Pro Gly Ser Tyr Leu Ile Ser<br>               2485                   2490                   2495 | 7665 | |
| ATC AAG TAC GGC GGC CCC TAC CAC ATT GGG GGC AGC CCC TTC AAG GCC<br>Ile Lys Tyr Gly Gly Pro Tyr His Ile Gly Gly Ser Pro Phe Lys Ala<br>2500                   2505                   2510 | 7713 | |
| AAA GTC ACA GGC CCC CGT CTC GTC AGC AAC CAC AGC CTC CAC GAG ACA<br>Lys Val Thr Gly Pro Arg Leu Val Ser Asn His Ser Leu His Glu Thr<br>2515                   2520                   2525                   2530 | 7761 | |
| TCA TCA GTG TTT GTA GAC TCT CTG ACC AAG GCC ACC TGT GCC CCC CAG<br>Ser Ser Val Phe Val Asp Ser Leu Thr Lys Ala Thr Cys Ala Pro Gln<br>               2535                   2540                   2545 | 7809 | |
| CAT GGG GCC CCG GGT CCT GGG CCT GCT GAC GCC AGC AAG GTG GTG GCC<br>His Gly Ala Pro Gly Pro Gly Pro Ala Asp Ala Ser Lys Val Val Ala<br>        2550                       2555                   2560 | 7857 | |
| AAG GGC CTG GGG CTG AGC AAG GCC TAC GTA GGC CAG AAG AGC AGC TTC<br>Lys Gly Leu Gly Leu Ser Lys Ala Tyr Val Gly Gln Lys Ser Ser Phe<br>2565                   2570                   2575 | 7905 | |
| ACA GTA GAC TGC AGC AAA GCA GGC AAC AAC ATG CTG CTG GTG GGG GTT<br>Thr Val Asp Cys Ser Lys Ala Gly Asn Asn Met Leu Leu Val Gly Val<br>2580                   2585                   2590 | 7953 | |
| CAT GGC CCA AGG ACC CCC TGC GAG GAG ATC CTG GTG AAG CAC GTG GGC<br>His Gly Pro Arg Thr Pro Cys Glu Glu Ile Leu Val Lys His Val Gly<br>2595                   2600                   2605                   2610 | 8001 | |
| AGC CGG CTC TAC AGC GTG TCC TAC CTG CTC AAG GAC AAG GGG GAG TAC<br>Ser Arg Leu Tyr Ser Val Ser Tyr Leu Leu Lys Asp Lys Gly Glu Tyr<br>               2615                   2620                   2625 | 8049 | |
| ACA CTG GTG GTC AAA TGG GGG CAC GAG CAC ATC CCA GGC AGC CCC TAC<br>Thr Leu Val Val Lys Trp Gly His Glu His Ile Pro Gly Ser Pro Tyr<br>               2630                   2635                   2640 | 8097 | |
| CGC GTT GTG GTG CCC TGAGTCTGGG GCCCGTGCCA GCCGGCAGCC CCCAAGCCTG<br>Arg Val Val Val Pro<br>        2645 | 8152 | |

```
CCCCGCTACC CAAGCAGCCC CGCCCTCTTC CCCTCAACCC CGGCCCAGGC CGCCCTGGCC     8212

GCCCGCCTGT CACTGCAGCT GCCCCTGCCC TGTGCCGTGC TGCGCTCACC TGCCTCCCCA     8272

GCCAGCCGCT GACCTCTCGG CTTTCACTTG GGCAGAGGGA GCCATTTGGT GGCGCTGCTT     8332

GTCTTCTTTG GTTCTGGGAG GGGTGAGGGA TGGGG                                8367
```

(2) INFORMATION FOR SEQ ID NO:8:

(i) SEQUENCE CHARACTERISTICS:
        (A) LENGTH: 2647 amino acids
        (B) TYPE: amino acid
        (D) TOPOLOGY: linear (ii) MOLECULE TYPE: protein (xi) SEQUENCE DESCRIPTION: SEQ ID NO:8:

```
Met Ser Ser Ser His Ser Arg Ala Gly Gln Ser Ala Ala Gly Ala Ala
 1               5                   10                  15

Pro Gly Gly Gly Val Asp Thr Arg Asp Ala Glu Met Pro Ala Thr Glu
                20                  25                  30

Lys Asp Leu Ala Glu Asp Ala Pro Trp Lys Lys Ile Gln Gln Asn Thr
            35                  40                  45

Phe Thr Arg Trp Cys Asn Glu His Leu Lys Cys Val Ser Lys Arg Ile
        50                  55                  60

Ala Asn Leu Gln Thr Asp Leu Ser Asp Gly Leu Arg Leu Ile Ala Leu
65                  70                  75                  80

Leu Glu Val Leu Ser Gln Lys Lys Met His Arg Lys His Asn Gln Arg
                85                  90                  95

Pro Thr Phe Arg Gln Met Gln Leu Glu Asn Val Ser Val Ala Leu Glu
            100                 105                 110

Phe Leu Asp Arg Glu Ser Ile Lys Leu Val Ser Ile Asp Ser Lys Ala
        115                 120                 125

Ile Val Asp Gly Asn Leu Lys Leu Ile Leu Gly Leu Ile Trp Thr Leu
130                 135                 140

Ile Leu His Tyr Ser Ile Ser Met Pro Met Trp Asp Glu Glu Glu Asp
145                 150                 155                 160

Glu Glu Ala Lys Lys Gln Thr Pro Lys Gln Arg Leu Leu Gly Trp Ile
                165                 170                 175

Gln Asn Lys Leu Pro Gln Leu Pro Ile Thr Asn Phe Ser Arg Asp Trp
            180                 185                 190

Gln Ser Gly Arg Ala Leu Gly Ala Leu Val Asp Ser Cys Ala Pro Gly
        195                 200                 205

Leu Cys Pro Asp Trp Asp Ser Trp Asp Ala Ser Lys Pro Val Thr Asn
210                 215                 220

Ala Arg Glu Ala Met Gln Gln Ala Asp Asp Trp Leu Gly Ile Pro Gln
225                 230                 235                 240

Val Ile Thr Pro Glu Glu Ile Val Asp Pro Asn Val Asp Glu His Ser
                245                 250                 255

Val Met Thr Tyr Leu Ser Gln Phe Pro Lys Ala Lys Leu Lys Pro Gly
            260                 265                 270

Ala Pro Leu Arg Pro Lys Leu Asn Pro Lys Lys Ala Arg Ala Tyr Gly
        275                 280                 285

Pro Gly Ile Glu Pro Thr Gly Asn Met Val Lys Lys Arg Ala Glu Phe
290                 295                 300

Thr Val Glu Thr Arg Ser Ala Gly Gln Gly Glu Val Leu Val Tyr Val
305                 310                 315                 320
```

-continued

```
Glu Asp Pro Ala Gly His Gln Glu Ala Lys Val Thr Ala Asn Asn
            325                 330                 335

Asp Lys Asn Arg Thr Phe Ser Val Trp Tyr Val Pro Glu Val Thr Gly
            340                 345                 350

Thr His Lys Val Thr Val Leu Phe Ala Gly Gln His Ile Ala Lys Ser
            355                 360                 365

Pro Phe Glu Val Tyr Val Asp Lys Ser Gln Gly Asp Ala Ser Lys Val
            370                 375                 380

Thr Ala Gln Gly Pro Gly Leu Glu Pro Ser Gly Asn Ile Ala Asn Lys
385                 390                 395                 400

Thr Thr Tyr Phe Glu Ile Phe Thr Ala Gly Ala Gly Thr Gly Glu Val
                    405                 410                 415

Glu Val Val Ile Gln Asp Pro Met Gly Gln Lys Gly Thr Val Glu Pro
                420                 425                 430

Gln Leu Glu Ala Arg Gly Asp Ser Thr Tyr Arg Cys Ser Tyr Gln Pro
            435                 440                 445

Thr Met Glu Gly Val His Thr Val His Val Thr Phe Ala Gly Val Pro
            450                 455                 460

Ile Pro Arg Ser Pro Tyr Thr Val Thr Val Gly Gln Ala Cys Asn Pro
465                 470                 475                 480

Ser Ala Cys Arg Ala Val Gly Arg Gly Leu Gln Pro Lys Gly Val Arg
                    485                 490                 495

Val Lys Glu Thr Ala Asp Phe Lys Val Tyr Thr Lys Gly Ala Gly Ser
                500                 505                 510

Gly Glu Leu Lys Val Thr Val Lys Gly Pro Lys Gly Glu Glu Arg Val
            515                 520                 525

Lys Gln Lys Asp Leu Gly Asp Gly Val Tyr Gly Phe Glu Tyr Tyr Pro
            530                 535                 540

Met Val Pro Gly Thr Tyr Ile Val Thr Ile Thr Trp Gly Gly Gln Asn
545                 550                 555                 560

Ile Gly Arg Ser Pro Phe Glu Val Lys Val Gly Thr Glu Cys Gly Asn
                    565                 570                 575

Gln Lys Val Arg Ala Trp Gly Pro Gly Leu Glu Gly Gly Val Val Gly
                580                 585                 590

Lys Ser Ala Asp Phe Val Val Glu Ala Ile Gly Asp Asp Val Gly Thr
            595                 600                 605

Leu Gly Phe Ser Val Glu Gly Pro Ser Gln Ala Lys Ile Glu Cys Asp
            610                 615                 620

Asp Lys Gly Asp Gly Ser Cys Asp Val Arg Tyr Trp Pro Gln Glu Ala
625                 630                 635                 640

Gly Glu Tyr Ala Val His Val Leu Cys Asn Ser Glu Asp Ile Arg Leu
                    645                 650                 655

Ser Pro Phe Met Ala Asp Ile Arg Asp Ala Pro Gln Asp Phe His Pro
                660                 665                 670

Asp Arg Val Lys Ala Arg Gly Pro Gly Leu Glu Lys Thr Gly Val Ala
            675                 680                 685

Val Asn Lys Pro Ala Glu Phe Thr Val Asp Ala Lys His Gly Gly Lys
            690                 695                 700

Ala Pro Leu Arg Val Gln Val Gln Asp Asn Glu Gly Cys Pro Val Glu
705                 710                 715                 720

Ala Leu Val Lys Asp Asn Gly Asn Gly Thr Tyr Ser Cys Ser Tyr Val
                    725                 730                 735

Pro Arg Lys Pro Val Lys His Thr Ala Met Val Ser Trp Gly Gly Val
                740                 745                 750
```

-continued

```
Ser Ile Pro Asn Ser Pro Phe Arg Val Asn Val Gly Ala Gly Ser His
        755                 760                 765

Pro Asn Lys Val Lys Val Tyr Gly Pro Gly Val Ala Lys Thr Gly Leu
        770                 775                 780

Lys Ala His Glu Pro Thr Tyr Phe Thr Val Asp Cys Ala Glu Ala Gly
785                 790                 795                 800

Gln Gly Asp Val Ser Ile Gly Ile Lys Cys Ala Pro Gly Val Val Gly
                    805                 810                 815

Pro Ala Glu Ala Asp Ile Asp Phe Asp Ile Ile Arg Asn Asp Asn Asp
                820                 825                 830

Thr Phe Thr Val Lys Tyr Thr Pro Arg Gly Ala Gly Ser Tyr Thr Ile
            835                 840                 845

Met Val Leu Phe Ala Asp Gln Ala Thr Pro Thr Ser Pro Ile Arg Val
        850                 855                 860

Lys Val Glu Pro Ser His Asp Ala Ser Lys Val Lys Ala Glu Gly Pro
865                 870                 875                 880

Gly Leu Ser Arg Thr Gly Val Glu Leu Gly Lys Pro Thr His Phe Thr
                    885                 890                 895

Val Asn Ala Lys Ala Ala Gly Lys Gly Lys Leu Asp Val Gln Phe Ser
                900                 905                 910

Gly Leu Thr Lys Gly Asp Ala Val Arg Asp Val Asp Ile Ile Asp His
            915                 920                 925

His Asp Asn Thr Tyr Thr Val Lys Tyr Thr Pro Val Gln Gln Gly Pro
        930                 935                 940

Val Gly Val Asn Val Thr Tyr Gly Gly Asp Pro Ile Pro Lys Ser Pro
945                 950                 955                 960

Phe Ser Val Ala Val Ser Pro Ser Leu Asp Leu Ser Lys Ile Lys Val
                    965                 970                 975

Ser Gly Leu Gly Glu Lys Val Asp Val Gly Lys Asp Gln Glu Phe Thr
                980                 985                 990

Val Lys Ser Lys Gly Ala Gly Gly Gln Gly Lys Val Ala Ser Lys Ile
            995                 1000                1005

Val Gly Pro Ser Gly Ala Ala Val Pro Cys Lys Val Glu Pro Gly Leu
        1010                1015                1020

Gly Ala Asp Asn Ser Val Val Arg Phe Leu Pro Arg Glu Glu Gly Pro
1025                1030                1035                1040

Tyr Glu Val Glu Val Thr Tyr Asp Gly Val Pro Val Pro Gly Ser Pro
                    1045                1050                1055

Phe Pro Leu Glu Ala Val Ala Pro Thr Lys Pro Ser Lys Val Lys Ala
                1060                1065                1070

Phe Gly Pro Gly Leu Gln Gly Gly Ser Ala Gly Ser Pro Ala Arg Phe
            1075                1080                1085

Thr Ile Asp Thr Lys Gly Ala Gly Thr Gly Gly Leu Gly Leu Thr Val
        1090                1095                1100

Glu Gly Pro Cys Glu Ala Gln Leu Glu Cys Leu Asp Asn Gly Asp Gly
1105                1110                1115                1120

Thr Cys Ser Val Ser Tyr Val Pro Thr Glu Pro Gly Asp Tyr Asn Ile
                    1125                1130                1135

Asn Ile Leu Phe Ala Asp Thr His Ile Pro Gly Ser Pro Phe Lys Ala
                1140                1145                1150

His Val Val Pro Cys Phe Asp Ala Ser Lys Val Lys Cys Ser Gly Pro
            1155                1160                1165

Gly Leu Glu Arg Ala Thr Ala Gly Glu Val Gly Gln Phe Gln Val Asp
```

-continued

```
           1170                1175                1180
Cys Ser Ser Ala Gly Ser Ala Glu Leu Thr Ile Glu Ile Cys Ser Glu
1185                1190                1195                1200
Ala Gly Leu Pro Ala Glu Val Tyr Ile Gln Asp His Gly Asp Gly Thr
                    1205                1210                1215
His Thr Ile Thr Tyr Ile Pro Leu Cys Pro Gly Ala Tyr Thr Val Thr
                    1220                1225                1230
Ile Lys Tyr Gly Gly Gln Pro Val Pro Asn Phe Pro Ser Lys Leu Gln
                    1235                1240                1245
Val Glu Pro Ala Val Asp Thr Ser Gly Val Gln Cys Tyr Gly Pro Gly
1250                    1255                1260
Ile Glu Gly Gln Gly Val Phe Arg Glu Ala Thr Thr Glu Phe Ser Val
1265                1270                1275                1280
Asp Ala Arg Ala Leu Thr Gln Thr Gly Gly Pro His Val Lys Ala Arg
                    1285                1290                1295
Val Ala Asn Pro Ser Gly Asn Leu Thr Glu Thr Tyr Val Gln Asp Arg
                    1300                1305                1310
Gly Asp Gly Met Tyr Lys Val Glu Tyr Thr Pro Tyr Glu Glu Gly Leu
                    1315                1320                1325
His Ser Val Asp Val Thr Tyr Asp Gly Ser Pro Val Pro Ser Ser Pro
                    1330                1335                1340
Phe Gln Val Pro Val Thr Glu Gly Cys Asp Pro Ser Arg Val Arg Val
1345                1350                1355                1360
His Gly Pro Gly Ile Gln Ser Gly Thr Thr Asn Lys Pro Asn Lys Phe
                    1365                1370                1375
Thr Val Glu Thr Arg Gly Ala Gly Thr Gly Gly Leu Gly Leu Ala Val
                    1380                1385                1390
Glu Gly Pro Ser Glu Ala Lys Met Ser Cys Met Asp Asn Lys Asp Gly
                    1395                1400                1405
Ser Cys Ser Val Glu Tyr Ile Pro Tyr Glu Ala Gly Thr Tyr Ser Leu
                    1410                1415                1420
Asn Val Thr Tyr Gly Gly His Gln Val Pro Gly Ser Pro Phe Lys Val
1425                1430                1435                1440
Pro Val His Asp Val Thr Asp Ala Ser Lys Val Lys Cys Ser Gly Pro
                    1445                1450                1455
Gly Leu Ser Pro Gly Met Val Arg Ala Asn Leu Pro Gln Ser Phe Gln
                    1460                1465                1470
Val Asp Thr Ser Lys Ala Gly Val Ala Pro Leu Gln Val Lys Val Gln
                    1475                1480                1485
Gly Pro Lys Gly Leu Val Glu Pro Val Asp Val Asp Asn Ala Asp
                    1490                1495                1500
Gly Thr Gln Thr Val Asn Tyr Val Pro Ser Arg Glu Gly Pro Tyr Ser
1505                1510                1515                1520
Ile Ser Val Leu Tyr Gly Asp Glu Glu Val Pro Arg Ser Pro Phe Lys
                    1525                1530                1535
Val Lys Val Leu Pro Thr His Asp Ala Ser Lys Val Lys Ala Ser Gly
                    1540                1545                1550
Pro Gly Leu Asn Thr Thr Gly Val Pro Ala Ser Leu Pro Val Glu Phe
                    1555                1560                1565
Thr Ile Asp Ala Lys Asp Ala Gly Glu Gly Leu Leu Ala Val Gln Ile
                    1570                1575                1580
Thr Asp Pro Glu Gly Lys Pro Lys Lys Thr His Ile Gln Asp Asn His
1585                1590                1595                1600
```

-continued

Asp Gly Thr Tyr Thr Val Ala Tyr Val Pro Asp Val Thr Gly Arg Tyr
            1605                1610                1615

Thr Ile Leu Ile Lys Tyr Gly Gly Asp Glu Ile Pro Phe Ser Pro Tyr
            1620                1625                1630

Arg Val Arg Ala Val Pro Thr Gly Asp Ala Ser Lys Cys Thr Val Thr
            1635                1640                1645

Val Ser Ile Gly Gly His Gly Leu Gly Ala Gly Ile Gly Pro Thr Ile
            1650                1655                1660

Gln Ile Gly Glu Glu Thr Val Ile Thr Val Asp Thr Lys Ala Ala Gly
1665                1670                1675                1680

Lys Gly Lys Val Thr Cys Thr Val Cys Thr Pro Asp Gly Ser Glu Val
                1685                1690                1695

Asp Val Asp Val Val Glu Asn Glu Asp Gly Thr Phe Asp Ile Phe Tyr
            1700                1705                1710

Thr Ala Pro Gln Pro Gly Lys Tyr Val Ile Cys Val Arg Phe Gly Gly
            1715                1720                1725

Glu His Val Pro Asn Ser Pro Phe Gln Val Thr Ala Leu Ala Gly Asp
            1730                1735                1740

Gln Pro Ser Val Gln Pro Leu Arg Ser Gln Gln Leu Ala Pro Gln
1745                1750                1755                1760

Tyr Thr Tyr Ala Gln Gly Gly Gln Gln Thr Trp Ala Pro Glu Arg Pro
            1765                1770                1775

Leu Val Gly Val Asn Gly Leu Asp Val Thr Ser Leu Arg Pro Phe Asp
            1780                1785                1790

Leu Val Ile Pro Phe Thr Ile Lys Lys Gly Glu Ile Thr Gly Glu Val
            1795                1800                1805

Arg Met Pro Ser Gly Lys Val Ala Gln Pro Thr Ile Thr Asp Asn Lys
            1810                1815                1820

Asp Gly Thr Val Thr Val Arg Tyr Ala Pro Ser Glu Ala Gly Leu His
1825                1830                1835                1840

Glu Met Asp Ile Arg Tyr Asp Asn Met His Ile Pro Gly Ser Pro Leu
            1845                1850                1855

Gln Phe Tyr Val Asp Tyr Val Asn Cys Gly His Val Thr Ala Tyr Gly
            1860                1865                1870

Pro Gly Leu Thr His Gly Val Val Asn Lys Pro Ala Thr Phe Thr Val
            1875                1880                1885

Asn Thr Lys Asp Ala Gly Glu Gly Gly Leu Ser Leu Ala Ile Glu Gly
            1890                1895                1900

Pro Ser Lys Ala Glu Ile Ser Cys Thr Asp Asn Gln Asp Gly Thr Cys
1905                1910                1915                1920

Ser Val Ser Tyr Leu Pro Val Leu Pro Gly Asp Tyr Ser Ile Leu Val
                1925                1930                1935

Lys Tyr Asn Glu Gln His Val Pro Gly Ser Pro Phe Thr Ala Arg Val
            1940                1945                1950

Thr Gly Asp Asp Ser Met Arg Met Ser His Leu Lys Val Gly Ser Ala
            1955                1960                1965

Ala Asp Ile Pro Ile Asn Ile Ser Glu Thr Asp Leu Ser Leu Leu Thr
            1970                1975                1980

Ala Thr Val Val Pro Pro Ser Gly Arg Glu Glu Pro Cys Leu Leu Lys
1985                1990                1995                2000

Arg Leu Arg Asn Gly His Val Gly Ile Ser Phe Val Pro Lys Glu Thr
                2005                2010                2015

Gly Glu His Leu Val His Val Lys Lys Asn Gly Gln His Val Ala Ser
            2020                2025                2030

```
Ser Pro Ile Pro Val Val Ile Ser Gln Ser Glu Ile Gly Asp Ala Ser
        2035                2040                2045

Arg Val Arg Val Ser Gly Gln Gly Leu His Glu Gly His Thr Phe Glu
            2050                2055                2060

Pro Ala Glu Phe Ile Ile Asp Thr Arg Asp Ala Gly Tyr Gly Gly Leu
2065                2070                2075                2080

Ser Leu Ser Ile Glu Gly Pro Ser Lys Val Asp Ile Asn Thr Glu Asp
                2085                2090                2095

Leu Glu Asp Gly Thr Cys Arg Val Thr Tyr Cys Pro Thr Glu Pro Gly
            2100                2105                2110

Asn Tyr Ile Ile Asn Ile Lys Phe Ala Asp Gln His Val Pro Gly Ser
            2115                2120                2125

Pro Phe Ser Val Lys Val Thr Gly Glu Gly Arg Val Lys Glu Ser Ile
            2130                2135                2140

Thr Arg Arg Arg Arg Ala Pro Ser Val Ala Asn Val Gly Ser His Cys
2145                2150                2155                2160

Asp Leu Ser Leu Lys Ile Pro Glu Ile Ser Ile Gln Asp Met Thr Ala
            2165                2170                2175

Gln Val Thr Ser Pro Ser Gly Lys Thr His Glu Ala Glu Ile Val Glu
            2180                2185                2190

Gly Glu Asn His Thr Tyr Cys Ile Arg Phe Val Pro Ala Glu Met Gly
            2195                2200                2205

Thr His Thr Val Ser Val Lys Tyr Lys Gly Gln His Val Pro Gly Ser
            2210                2215                2220

Pro Phe Gln Phe Thr Val Gly Pro Leu Gly Glu Gly Gly Ala His Lys
2225                2230                2235                2240

Val Arg Ala Gly Gly Pro Gly Leu Glu Arg Ala Glu Ala Gly Val Pro
            2245                2250                2255

Ala Glu Phe Ser Ile Trp Thr Arg Glu Ala Gly Ala Gly Gly Leu Ala
            2260                2265                2270

Ile Ala Val Glu Gly Pro Ser Lys Ala Glu Ile Ser Phe Glu Asp Arg
            2275                2280                2285

Lys Asp Gly Ser Cys Gly Val Ala Tyr Val Val Gln Glu Pro Gly Asp
            2290                2295                2300

Tyr Glu Val Ser Val Lys Phe Asn Glu Glu His Ile Pro Asp Ser Pro
2305                2310                2315                2320

Phe Val Val Pro Val Ala Ser Pro Ser Gly Asp Ala Arg Arg Leu Thr
            2325                2330                2335

Val Ser Ser Leu Gln Glu Ser Gly Leu Lys Val Asn Gln Pro Ala Ser
            2340                2345                2350

Phe Ala Val Ser Leu Asn Gly Ala Lys Gly Ala Ile Asp Ala Lys Val
            2355                2360                2365

His Ser Pro Ser Gly Ala Leu Glu Glu Cys Tyr Val Thr Glu Ile Asp
            2370                2375                2380

Gln Asp Lys Tyr Ala Val Arg Phe Ile Pro Arg Glu Asn Gly Val Tyr
2385                2390                2395                2400

Leu Ile Asp Val Lys Phe Asn Gly Thr His Ile Pro Gly Ser Pro Phe
            2405                2410                2415

Lys Ile Arg Val Gly Glu Pro Gly His Gly Gly Asp Pro Gly Leu Val
            2420                2425                2430

Ser Ala Tyr Gly Ala Gly Leu Glu Gly Gly Val Thr Gly Asn Pro Ala
            2435                2440                2445

Glu Phe Val Val Asn Thr Ser Asn Ala Gly Ala Gly Ala Leu Ser Val
```

```
            2450                2455                2460
Thr Ile Asp Gly Pro Ser Lys Val Lys Met Asp Cys Gln Glu Cys Pro
2465                2470                2475                2480

Glu Gly Tyr Arg Val Thr Tyr Thr Pro Met Ala Pro Gly Ser Tyr Leu
            2485                2490                2495

Ile Ser Ile Lys Tyr Gly Gly Pro Tyr His Ile Gly Gly Ser Pro Phe
            2500                2505                2510

Lys Ala Lys Val Thr Gly Pro Arg Leu Val Ser Asn His Ser Leu His
            2515                2520                2525

Glu Thr Ser Ser Val Phe Val Asp Ser Leu Thr Lys Ala Thr Cys Ala
            2530                2535                2540

Pro Gln His Gly Ala Pro Gly Pro Gly Pro Ala Asp Ala Ser Lys Val
2545                2550                2555                2560

Val Ala Lys Gly Leu Gly Leu Ser Lys Ala Tyr Val Gly Gln Lys Ser
            2565                2570                2575

Ser Phe Thr Val Asp Cys Ser Lys Ala Gly Asn Asn Met Leu Leu Val
            2580                2585                2590

Gly Val His Gly Pro Arg Thr Pro Cys Glu Glu Ile Leu Val Lys His
            2595                2600                2605

Val Gly Ser Arg Leu Tyr Ser Val Ser Tyr Leu Leu Lys Asp Lys Gly
            2610                2615                2620

Glu Tyr Thr Leu Val Val Lys Trp Gly His Glu His Ile Pro Gly Ser
2625                2630                2635                2640

Pro Tyr Arg Val Val Val Pro
            2645
```

(2) INFORMATION FOR SEQ ID NO:9:

(i) SEQUENCE CHARACTERISTICS:
        (A) LENGTH: 1125 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1125

(xi) SEQUENCE DESCRIPTION: SEQ ID NO:9:

```
TTC GAG ATG TCT GAC TTC ATC GTG GAC ACA AGG GAT GCA GGT TAT GGT      48
Phe Glu Met Ser Asp Phe Ile Val Asp Thr Arg Asp Ala Gly Tyr Gly
  1               5                  10                  15

GGC ATA TCC TTG GCG GTG GAA GGC CCC AGC AAA GTG GAC ATC CAG ACG      96
Gly Ile Ser Leu Ala Val Glu Gly Pro Ser Lys Val Asp Ile Gln Thr
             20                  25                  30

GAG GAC CTG GAA GAT GGC ACC TGC AAA GTC TCC TAC TTC CCT ACC GTG     144
Glu Asp Leu Glu Asp Gly Thr Cys Lys Val Ser Tyr Phe Pro Thr Val
         35                  40                  45

CCT GGG GTT TAT ATC GTC TCC ACC AAA TTC GCT GAC GAG CAC GTG CCT     192
Pro Gly Val Tyr Ile Val Ser Thr Lys Phe Ala Asp Glu His Val Pro
     50                  55                  60

GGG AGC CCA TTT ACC GTG AAG ATC AGT GGG GAG GGA AGA GTC AAA GAG     240
Gly Ser Pro Phe Thr Val Lys Ile Ser Gly Glu Gly Arg Val Lys Glu
 65                  70                  75                  80

AGC ATC ACC CGC ACC AGT CGG GCC CCG TCC GTG GCC ACT GTC GGG AGC     288
Ser Ile Thr Arg Thr Ser Arg Ala Pro Ser Val Ala Thr Val Gly Ser
                 85                  90                  95

ATT TGT GAC CTG AAC CTC AAA ATC CCA GAA ATC AAC AGC AGT GAT ATG     336
```

| | | | | | | | | | | | | | |
|---|---|---|---|---|---|---|---|---|---|---|---|---|---|
| Ile | Cys | Asp | Leu | Asn | Leu | Lys | Ile | Pro | Glu | Ile | Asn | Ser | Ser | Asp | Met |
| | | | 100 | | | | 105 | | | | 110 | | |

```
TCG GCC CAC GTC ACC AGC CCC TCT GGC CGT GTG ACT GAG GCA GAG ATT        384
Ser Ala His Val Thr Ser Pro Ser Gly Arg Val Thr Glu Ala Glu Ile
    115                 120                 125

GTG CCC ATG GGG AAG AAC TCA CAC TGC GTC CGG TTT GTG CCC CAG GAG        432
Val Pro Met Gly Lys Asn Ser His Cys Val Arg Phe Val Pro Gln Glu
130                 135                 140

ATG GGC GTG CAC ACG GTC AGC GTC AAG TAC CGT GGG CAG CAC GTC ACC        480
Met Gly Val His Thr Val Ser Val Lys Tyr Arg Gly Gln His Val Thr
145                 150                 155                 160

GGC AGC CCC TTC CAG TTC ACC GTG GGG GCA CTT GGT GAA GGA GGC GCC        528
Gly Ser Pro Phe Gln Phe Thr Val Gly Ala Leu Gly Glu Gly Gly Ala
                165                 170                 175

CAC AAG GTG CGG GCA GGA GGC CCT GGC CTG GAG AGA GGA GAA GCG GGA        576
His Lys Val Arg Ala Gly Gly Pro Gly Leu Glu Arg Gly Glu Ala Gly
            180                 185                 190

GTC CCA GCT GAG TTC AGC ATT TGG ACC CGG GAA GCA GGC GCT GGA GGC        624
Val Pro Ala Glu Phe Ser Ile Trp Thr Arg Glu Ala Gly Ala Gly Gly
        195                 200                 205

CTC TCC ATC GCT GTT GAG GGC CCC AGT AAG GCC GAG ATT ACA TTC GAT        672
Leu Ser Ile Ala Val Glu Gly Pro Ser Lys Ala Glu Ile Thr Phe Asp
210                 215                 220

GAC CAT AAA AAT GGG TCG TGC GGT GTA TCT TAT ATT GCC CAA GAG CCT        720
Asp His Lys Asn Gly Ser Cys Gly Val Ser Tyr Ile Ala Gln Glu Pro
225                 230                 235                 240

GGT AAC TAC GAG GTG TCC ATC AAG TTC AAT GAT GAG CAC ATC CCG GAA        768
Gly Asn Tyr Glu Val Ser Ile Lys Phe Asn Asp Glu His Ile Pro Glu
                245                 250                 255

AGC CCC TAC CTG GTG CCG GTC ATC GCA CCC TCC GAC GAC GCC CGC CGC        816
Ser Pro Tyr Leu Val Pro Val Ile Ala Pro Ser Asp Asp Ala Arg Arg
            260                 265                 270

CTC ACT GTT ATG AGC CTT CAG GAA TCG GGA TTA AAA GTT AAC CAG CCA        864
Leu Thr Val Met Ser Leu Gln Glu Ser Gly Leu Lys Val Asn Gln Pro
        275                 280                 285

GCA TCC TTT GCT ATA AGG TTG AAT GGC GCA AAA GGC AAG ATT GAT GCA        912
Ala Ser Phe Ala Ile Arg Leu Asn Gly Ala Lys Gly Lys Ile Asp Ala
290                 295                 300

AAG GTG CAC AGC CCC TCT GGA GCC GTG GAG GAG TGC CAC GTG TCT GAG        960
Lys Val His Ser Pro Ser Gly Ala Val Glu Glu Cys His Val Ser Glu
305                 310                 315                 320

CTG GAG CCA GAT AAG TAT GCT GTT CGC TTC ATC CCT CAT GAG AAT GGT       1008
Leu Glu Pro Asp Lys Tyr Ala Val Arg Phe Ile Pro His Glu Asn Gly
                325                 330                 335

GTC CAC ACC ATC GAT GTC AAG TTC AAT GGG AGC CAC GTG GTT GGA AGC       1056
Val His Thr Ile Asp Val Lys Phe Asn Gly Ser His Val Val Gly Ser
            340                 345                 350

CCC TTC AAA GTG CGC GTT GGG GAG CCT GGA CAA GCG GGG AAC CCT GCC       1104
Pro Phe Lys Val Arg Val Gly Glu Pro Gly Gln Ala Gly Asn Pro Ala
        355                 360                 365

CTG GTG TCC GCC TAT GGC ACG                                           1125
Leu Val Ser Ala Tyr Gly Thr
370                 375
```

(2) INFORMATION FOR SEQ ID NO:10:

(i) SEQUENCE CHARACTERISTICS:
        (A) LENGTH: 375 amino acids
        (B) TYPE: amino acid
        (D) TOPOLOGY: linear (ii) MOLECULE TYPE: protein (xi) SEQUENCE DESCRIPTION: SEQ ID NO:10:

```
Phe Glu Met Ser Asp Phe Ile Val Asp Thr Arg Asp Ala Gly Tyr Gly
 1               5                  10                  15

Gly Ile Ser Leu Ala Val Glu Gly Pro Ser Lys Val Asp Ile Gln Thr
             20                  25                  30

Glu Asp Leu Glu Asp Gly Thr Cys Lys Val Ser Tyr Phe Pro Thr Val
             35                  40                  45

Pro Gly Val Tyr Ile Val Ser Thr Lys Phe Ala Asp Glu His Val Pro
         50                  55                  60

Gly Ser Pro Phe Thr Val Lys Ile Ser Gly Glu Gly Arg Val Lys Glu
 65                  70                  75                  80

Ser Ile Thr Arg Thr Ser Arg Ala Pro Ser Val Ala Thr Val Gly Ser
             85                  90                  95

Ile Cys Asp Leu Asn Leu Lys Ile Pro Glu Ile Asn Ser Ser Asp Met
            100                 105                 110

Ser Ala His Val Thr Ser Pro Ser Gly Arg Val Thr Glu Ala Glu Ile
            115                 120                 125

Val Pro Met Gly Lys Asn Ser His Cys Val Arg Phe Val Pro Gln Glu
        130                 135                 140

Met Gly Val His Thr Val Ser Val Lys Tyr Arg Gly Gln His Val Thr
145                 150                 155                 160

Gly Ser Pro Phe Gln Phe Thr Val Gly Ala Leu Gly Glu Gly Gly Ala
            165                 170                 175

His Lys Val Arg Ala Gly Gly Pro Gly Leu Glu Arg Gly Glu Ala Gly
            180                 185                 190

Val Pro Ala Glu Phe Ser Ile Trp Thr Arg Glu Ala Gly Ala Gly Gly
        195                 200                 205

Leu Ser Ile Ala Val Glu Gly Pro Ser Lys Ala Glu Ile Thr Phe Asp
210                 215                 220

Asp His Lys Asn Gly Ser Cys Gly Val Ser Tyr Ile Ala Gln Glu Pro
225                 230                 235                 240

Gly Asn Tyr Glu Val Ser Ile Lys Phe Asn Asp Glu His Ile Pro Glu
            245                 250                 255

Ser Pro Tyr Leu Val Pro Val Ile Ala Pro Ser Asp Asp Ala Arg Arg
            260                 265                 270

Leu Thr Val Met Ser Leu Gln Glu Ser Gly Leu Lys Val Asn Gln Pro
        275                 280                 285

Ala Ser Phe Ala Ile Arg Leu Asn Gly Ala Lys Gly Lys Ile Asp Ala
290                 295                 300

Lys Val His Ser Pro Ser Gly Ala Val Glu Glu Cys His Val Ser Glu
305                 310                 315                 320

Leu Glu Pro Asp Lys Tyr Ala Val Arg Phe Ile Pro His Glu Asn Gly
            325                 330                 335

Val His Thr Ile Asp Val Lys Phe Asn Gly Ser His Val Val Gly Ser
        340                 345                 350

Pro Phe Lys Val Arg Val Gly Glu Pro Gly Gln Ala Gly Asn Pro Ala
            355                 360                 365

Leu Val Ser Ala Tyr Gly Thr
370                 375
```

(2) INFORMATION FOR SEQ ID NO:11:

(i) SEQUENCE CHARACTERISTICS:
        (A) LENGTH: 1494 base pairs (B) TYPE: nucleic acid
(C) STRANDEDNESS: single
(D) TOPOLOGY: linear (ii) MOLECULE TYPE: cDNA (ix) FEATURE:
(A) NAME/KEY: CDS
(B) LOCATION: 1..1449

(xi) SEQUENCE DESCRIPTION: SEQ ID NO:11:

| | | | | | | | | | | | | | | | | |
|---|---|---|---|---|---|---|---|---|---|---|---|---|---|---|---|---|
| AAA | ATC | CCA | GAA | ATC | AAC | AGC | AGT | GAT | ATG | TCG | GCC | CAC | GTC | ACC | AGC | 48 |
| Lys | Ile | Pro | Glu | Ile | Asn | Ser | Ser | Asp | Met | Ser | Ala | His | Val | Thr | Ser | |
| 1 | | | | 5 | | | | | 10 | | | | | 15 | | |
| CCC | TCT | GGC | CGT | GTG | ACT | GAG | GCA | GAG | ATT | GTG | CCC | ATG | GGG | AAG | AAC | 96 |
| Pro | Ser | Gly | Arg | Val | Thr | Glu | Ala | Glu | Ile | Val | Pro | Met | Gly | Lys | Asn | |
| | | | 20 | | | | | 25 | | | | | 30 | | | |
| TCA | CAC | TGC | GTC | CGG | TTT | GTG | CCC | CAG | GAG | ATG | GGC | GTG | CAC | ACG | GTC | 144 |
| Ser | His | Cys | Val | Arg | Phe | Val | Pro | Gln | Glu | Met | Gly | Val | His | Thr | Val | |
| | | 35 | | | | | 40 | | | | | 45 | | | | |
| AGC | GTC | AAG | TAC | CGT | GGG | CAG | CAC | GTC | ACC | GGC | AGC | CCC | TTC | CAG | TTC | 192 |
| Ser | Val | Lys | Tyr | Arg | Gly | Gln | His | Val | Thr | Gly | Ser | Pro | Phe | Gln | Phe | |
| | 50 | | | | | 55 | | | | | 60 | | | | | |
| ACC | GTG | GGG | GCA | CTT | GGT | GAA | GGA | GGC | GCC | CAC | AAG | GTG | CGG | GCA | GGA | 240 |
| Thr | Val | Gly | Ala | Leu | Gly | Glu | Gly | Gly | Ala | His | Lys | Val | Arg | Ala | Gly | |
| 65 | | | | 70 | | | | | 75 | | | | | 80 | | |
| GGC | CCT | GGC | CTG | GAG | AGA | GGA | GAA | GCG | GGA | GTC | CCA | GCT | GAG | TTC | AGC | 288 |
| Gly | Pro | Gly | Leu | Glu | Arg | Gly | Glu | Ala | Gly | Val | Pro | Ala | Glu | Phe | Ser | |
| | | | | 85 | | | | | 90 | | | | | 95 | | |
| ATT | TGG | ACC | CGG | GAA | GCA | GGC | GCT | GGA | GGC | CTC | TCC | ATC | GCT | GTT | GAG | 336 |
| Ile | Trp | Thr | Arg | Glu | Ala | Gly | Ala | Gly | Gly | Leu | Ser | Ile | Ala | Val | Glu | |
| | | | 100 | | | | | 105 | | | | | 110 | | | |
| GGC | CCC | AGT | AAG | GCC | GAG | ATT | ACA | TTC | GAT | GAC | CAT | AAA | AAT | GGG | TCG | 384 |
| Gly | Pro | Ser | Lys | Ala | Glu | Ile | Thr | Phe | Asp | Asp | His | Lys | Asn | Gly | Ser | |
| | | 115 | | | | | 120 | | | | | 125 | | | | |
| TGC | GGT | GTA | TCT | TAT | ATT | GCC | CAA | GAG | CCT | GGT | AAC | TAC | GAG | GTG | TCC | 432 |
| Cys | Gly | Val | Ser | Tyr | Ile | Ala | Gln | Glu | Pro | Gly | Asn | Tyr | Glu | Val | Ser | |
| | 130 | | | | | 135 | | | | | 140 | | | | | |
| ATC | AAG | TTC | AAT | GAT | GAG | CAC | ATC | CCG | GAA | AGC | CCC | TAC | CTG | GTG | CCG | 480 |
| Ile | Lys | Phe | Asn | Asp | Glu | His | Ile | Pro | Glu | Ser | Pro | Tyr | Leu | Val | Pro | |
| 145 | | | | 150 | | | | | 155 | | | | | 160 | | |
| GTC | ATC | GCA | CCC | TCC | GAC | GAC | GCC | CGC | CGC | CTC | ACT | GTT | ATG | AGC | CTT | 528 |
| Val | Ile | Ala | Pro | Ser | Asp | Asp | Ala | Arg | Arg | Leu | Thr | Val | Met | Ser | Leu | |
| | | | | 165 | | | | | 170 | | | | | 175 | | |
| CAG | GAA | TCG | GGA | TTA | AAA | GTT | AAC | CAG | CCA | GCA | TCC | TTT | GCT | ATA | AGG | 576 |
| Gln | Glu | Ser | Gly | Leu | Lys | Val | Asn | Gln | Pro | Ala | Ser | Phe | Ala | Ile | Arg | |
| | | | 180 | | | | | 185 | | | | | 190 | | | |
| TTG | AAT | GGC | GCA | AAA | GGC | AAG | ATT | GAT | GCA | AAG | GTG | CAC | AGC | CCC | TCT | 624 |
| Leu | Asn | Gly | Ala | Lys | Gly | Lys | Ile | Asp | Ala | Lys | Val | His | Ser | Pro | Ser | |
| | | 195 | | | | | 200 | | | | | 205 | | | | |
| GGA | GCC | GTG | GAG | GAG | TGC | CAC | GTG | TCT | GAG | CTG | GAG | CCA | GAT | AAG | TAT | 672 |
| Gly | Ala | Val | Glu | Glu | Cys | His | Val | Ser | Glu | Leu | Glu | Pro | Asp | Lys | Tyr | |
| | 210 | | | | | 215 | | | | | 220 | | | | | |
| GCT | GTT | CGC | TTC | ATC | CCT | CAT | GAG | AAT | GGT | GTC | CAC | ACC | ATC | GAT | GTC | 720 |
| Ala | Val | Arg | Phe | Ile | Pro | His | Glu | Asn | Gly | Val | His | Thr | Ile | Asp | Val | |
| 225 | | | | 230 | | | | | 235 | | | | | 240 | | |
| AAG | TTC | AAT | GGG | AGC | CAC | GTG | GTT | GGA | AGC | CCC | TTC | AAA | GTG | CGC | GTT | 768 |
| Lys | Phe | Asn | Gly | Ser | His | Val | Val | Gly | Ser | Pro | Phe | Lys | Val | Arg | Val | |
| | | | | 245 | | | | | 250 | | | | | 255 | | |
| GGG | GAG | CCT | GGA | CAA | GCG | GGG | AAC | CCT | GCC | CTG | GTG | TCC | GCC | TAT | GGC | 816 |
| Gly | Glu | Pro | Gly | Gln | Ala | Gly | Asn | Pro | Ala | Leu | Val | Ser | Ala | Tyr | Gly | |
| | | | 260 | | | | | 265 | | | | | 270 | | | |

```
ACG GGA CTC GAA GGG GGN ACC ACA GGT ATC CAG TCG GAA TTC TTT ATT        864
Thr Gly Leu Glu Gly Xaa Thr Thr Gly Ile Gln Ser Glu Phe Phe Ile
            275                 280                 285

AAC ACC ACC CGA GCA GGT CCA GGG ACA TTA TCC GTC ACC ATC GAA GGC        912
Asn Thr Thr Arg Ala Gly Pro Gly Thr Leu Ser Val Thr Ile Glu Gly
290                 295                 300

CCA TCC AAG GTT AAA ATG GAT TGC CAG GAA ACA CCT GAA GGG TAC AAA        960
Pro Ser Lys Val Lys Met Asp Cys Gln Glu Thr Pro Glu Gly Tyr Lys
305                 310                 315                 320

GTC ATG TAC ACC CCC ATG GCT CCT GGT AAC TAC CTG ATC AGT GTC AAA       1008
Val Met Tyr Thr Pro Met Ala Pro Gly Asn Tyr Leu Ile Ser Val Lys
                325                 330                 335

TAC GGT GGG CCC AAC CAC ATC GTG GGC AGT CCC TTC AAG GCC AAG GTG       1056
Tyr Gly Gly Pro Asn His Ile Val Gly Ser Pro Phe Lys Ala Lys Val
            340                 345                 350

ACT GGC CAG CGT CTA GTT AGC CCT GGC TCA GCC AAC GAG ACC TCA TCC       1104
Thr Gly Gln Arg Leu Val Ser Pro Gly Ser Ala Asn Glu Thr Ser Ser
        355                 360                 365

ATC CTG GTG GAG TCA GTG ACC AGG TCG TCT ACA GAG ACC TGC TAT AGC       1152
Ile Leu Val Glu Ser Val Thr Arg Ser Ser Thr Glu Thr Cys Tyr Ser
370                 375                 380

GCC ATT CCC AAG GCA TCC TCG GAC GCC AGC AAG GTG ACC TCT AAG GGG       1200
Ala Ile Pro Lys Ala Ser Ser Asp Ala Ser Lys Val Thr Ser Lys Gly
385                 390                 395                 400

GCA GGG CTC TCA AAG GCC TTT GTG GGC CAG AAG AGT TCC TTC CTG GTG       1248
Ala Gly Leu Ser Lys Ala Phe Val Gly Gln Lys Ser Ser Phe Leu Val
                405                 410                 415

GAC TGC AGC AAA GCT GGC TCC AAC ATG CTG CTG ATC GGG GTC CAT GGG       1296
Asp Cys Ser Lys Ala Gly Ser Asn Met Leu Leu Ile Gly Val His Gly
            420                 425                 430

CCC ACC ACC CCC TGC GAG GAG GTC TCC ATG AAG CAT GTA GGC AAC CAG       1344
Pro Thr Thr Pro Cys Glu Glu Val Ser Met Lys His Val Gly Asn Gln
        435                 440                 445

CAA TAC AAC GTC ACA TAC GTC GTC AAG GAG AGG GGC GAT TAT GTG CTG       1392
Gln Tyr Asn Val Thr Tyr Val Val Lys Glu Arg Gly Asp Tyr Val Leu
450                 455                 460

GCT GTG AAG TGG GGG GAG GAA CAC ATC CCT GGC AGC CCT TTT CAT GTC       1440
Ala Val Lys Trp Gly Glu Glu His Ile Pro Gly Ser Pro Phe His Val
465                 470                 475                 480

ACA GTG CCT TAAAACAGTT TTCTCAAATC CTGGAAAAAA AAAAAAAAAA AAAAA         1494
Thr Val Pro (2) INFORMATION FOR SEQ ID NO:12:

(i) SEQUENCE CHARACTERISTICS:
        (A) LENGTH: 483 amino acids
        (B) TYPE: amino acid
        (D) TOPOLOGY: linear (ii) MOLECULE TYPE: protein (xi) SEQUENCE DESCRIPTION: SEQ ID NO:12:

Lys Ile Pro Glu Ile Asn Ser Ser Asp Met Ser Ala His Val Thr Ser
1               5                   10                  15

Pro Ser Gly Arg Val Thr Glu Ala Glu Ile Val Pro Met Gly Lys Asn
            20                  25                  30

Ser His Cys Val Arg Phe Val Pro Gln Glu Met Gly Val His Thr Val
        35                  40                  45

Ser Val Lys Tyr Arg Gly Gln His Val Thr Gly Ser Pro Phe Gln Phe
    50                  55                  60

Thr Val Gly Ala Leu Gly Glu Gly Gly Ala His Lys Val Arg Ala Gly
```

-continued

```
            65                  70                  75                  80
Gly Pro Gly Leu Glu Arg Gly Glu Ala Gly Val Pro Ala Glu Phe Ser
                    85                  90                  95
Ile Trp Thr Arg Glu Ala Gly Ala Gly Gly Leu Ser Ile Ala Val Glu
                    100                 105                 110
Gly Pro Ser Lys Ala Glu Ile Thr Phe Asp Asp His Lys Asn Gly Ser
                    115                 120                 125
Cys Gly Val Ser Tyr Ile Ala Gln Glu Pro Gly Asn Tyr Glu Val Ser
                    130                 135                 140
Ile Lys Phe Asn Asp Glu His Ile Pro Glu Ser Pro Tyr Leu Val Pro
145                 150                 155                 160
Val Ile Ala Pro Ser Asp Asp Ala Arg Arg Leu Thr Val Met Ser Leu
                    165                 170                 175
Gln Glu Ser Gly Leu Lys Val Asn Gln Pro Ala Ser Phe Ala Ile Arg
                    180                 185                 190
Leu Asn Gly Ala Lys Gly Lys Ile Asp Ala Lys Val His Ser Pro Ser
                    195                 200                 205
Gly Ala Val Glu Glu Cys His Val Ser Glu Leu Glu Pro Asp Lys Tyr
                    210                 215                 220
Ala Val Arg Phe Ile Pro His Glu Asn Gly Val His Thr Ile Asp Val
225                 230                 235                 240
Lys Phe Asn Gly Ser His Val Val Gly Ser Pro Phe Lys Val Arg Val
                    245                 250                 255
Gly Glu Pro Gly Gln Ala Gly Asn Pro Ala Leu Val Ser Ala Tyr Gly
                    260                 265                 270
Thr Gly Leu Glu Gly Xaa Thr Thr Gly Ile Gln Ser Glu Phe Phe Ile
                    275                 280                 285
Asn Thr Thr Arg Ala Gly Pro Gly Thr Leu Ser Val Thr Ile Glu Gly
                    290                 295                 300
Pro Ser Lys Val Lys Met Asp Cys Gln Glu Thr Pro Glu Gly Tyr Lys
305                 310                 315                 320
Val Met Tyr Thr Pro Met Ala Pro Gly Asn Tyr Leu Ile Ser Val Lys
                    325                 330                 335
Tyr Gly Gly Pro Asn His Ile Val Gly Ser Pro Phe Lys Ala Lys Val
                    340                 345                 350
Thr Gly Gln Arg Leu Val Ser Pro Gly Ser Ala Asn Glu Thr Ser Ser
                    355                 360                 365
Ile Leu Val Glu Ser Val Thr Arg Ser Ser Thr Glu Thr Cys Tyr Ser
                    370                 375                 380
Ala Ile Pro Lys Ala Ser Ser Asp Ala Ser Lys Val Thr Ser Lys Gly
385                 390                 395                 400
Ala Gly Leu Ser Lys Ala Phe Val Gly Gln Lys Ser Ser Phe Leu Val
                    405                 410                 415
Asp Cys Ser Lys Ala Gly Ser Asn Met Leu Leu Ile Gly Val His Gly
                    420                 425                 430
Pro Thr Thr Pro Cys Glu Glu Val Ser Met Lys His Val Gly Asn Gln
                    435                 440                 445
Gln Tyr Asn Val Thr Tyr Val Val Lys Glu Arg Gly Asp Tyr Val Leu
                    450                 455                 460
Ala Val Lys Trp Gly Glu Glu His Ile Pro Gly Ser Pro Phe His Val
465                 470                 475                 480
Thr Val Pro
```

(2) INFORMATION FOR SEQ ID NO:13:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:13:

YRSVYDRRYS RKNWKDSNYK SATTTNRADS T                                    31

(2) INFORMATION FOR SEQ ID NO:14:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:14:

YRSVYDRRYS RKNWKDSN                                                  18

(2) INFORMATION FOR SEQ ID NO:15:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:

YRSVYDRRYS RKNWKDSNYK SA                                          22

(2) INFORMATION FOR SEQ ID NO:16:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:16:

YRSVYDRRYS RKNWKDSNYK SATTTN                                    26

(2) INFORMATION FOR SEQ ID NO:17:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:17:

YRSVYDRRYS RK                                                            12

(2) INFORMATION FOR SEQ ID NO:18:

(i) SEQUENCE CHARACTERISTICS:
        (A) LENGTH: 11 base pairs
        (B) TYPE: nucleic acid (C) STRANDEDNESS: single
        (D) TOPOLOGY: linear (ii) MOLECULE TYPE: cDNA (xi) SEQUENCE DESCRIPTION: SEQ ID NO:18:

YRSVYDRRYS R                                                                11

(2) INFORMATION FOR SEQ ID NO:19:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:19:

GATGGCACTT TTGTACTAAG GATTACTGTC CTG                                         33

(2) INFORMATION FOR SEQ ID NO:20:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:20:

ATTGATGGTG GTCGTCTAGG CACTTTTGTA GAG                                         33

(2) INFORMATION FOR SEQ ID NO:21:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:21:

GTCTGCCTCT TGAAACTAAG GATTGATGGT GGT                                         33

(2) INFORMATION FOR SEQ ID NO:22:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:22:

CCAGTTGAGT TGTTGCTACT CCTTCTCAAA GCG                                         33

(2) INFORMATION FOR SEQ ID NO:23:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:23:

GTTGCTGCTC CTTCTCCTAG CGACTGTATT CCCG                                    34

(2) INFORMATION FOR SEQ ID NO:24:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:24:

RAVYDRRYSR KNWKDSNYKS ATTTNRADST                                         30

(2) INFORMATION FOR SEQ ID NO:25:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:25:

RSVYDRRYSR KNWKDSNYKS ATTTNRADST                                         30

(2) INFORMATION FOR SEQ ID NO:26:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:26:

RSVYDARYSR KNWKDSNYKS ATTTNRADST                                         30

(2) INFORMATION FOR SEQ ID NO:27:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:27:

RSVYDRRYAR KNWKDSNYKS ATTTNRADST                                         30

(2) INFORMATION FOR SEQ ID NO:28:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:28:

GTCATAGATT TCCACCGCGA GCCGGTATCC GAG                                     33

(2) INFORMATION FOR SEQ ID NO:29:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:29:

CCGGCCGTCA TAGATTTGCA CCGAGAGCCG GTATC          35

(2) INFORMATION FOR SEQ ID NO:30:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:30:

GCGACTGTAT TCCCGCGCGT CATAGATTTC CAC          33

(2) INFORMATION FOR SEQ ID NO:31:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:31:

CTCCTTCTCA AAGCGCGCGT ATTCCCGGCG GTC          33

(2) INFORMATION FOR SEQ ID NO:32:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:32:

ATATCTCGAG AGTATACCCC CATGGCACCT          30

(2) INFORMATION FOR SEQ ID NO:33:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:33:

ATATCTCGAG TCAGGGCACC ACAACGCG          28

(2) INFORMATION FOR SEQ ID NO:34:

(i) SEQUENCE CHARACTERISTICS:
        (A) LENGTH: 32 base pairs
        (B) TYPE: nucleic acid

```
        (C) STRANDEDNESS: single
        (D) TOPOLOGY: linear (ii) MOLECULE TYPE: cDNA (xi) SEQUENCE DESCRIPTION: SEQ ID NO:34:

ATATCTCGAG TCAGCTGCTC TTCTGGCCCT AC                                      32

(2) INFORMATION FOR SEQ ID NO:35:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:35:

ATATCATATG TACACCCCCA TGGCTCCT                                           28

(2) INFORMATION FOR SEQ ID NO:36:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:36:

ATAGGATCCT CAGCCCCACA AACAGGC                                            27
```

CYTOPLASMIC MODULATORS OF INTEGRIN BINDING/SIGNALLING

BACKGROUND

A significant characteristic of the immune and inflammatory responses is the movement of leukocytes from the bloodstream into specific tissues in response to various physiological signals. For example, certain subsets of lymphocytes "home" to various secondary lymphoid tissues such as lymph nodes or Peyer's patches, and eventually return to circulation. Other leukocytes such as granulocytes and monocytes, however, do not return to circulation after transmigration from the bloodstream. Movement of leukocytes from circulation is effected by a series of receptor/counter-receptor interactions which are coordinated by various specific membrane adhesion molecules.

Extravasation of leukocytes from the bloodstream [for review, see McEver, *Curr. Opin. Cell Biol.* 4:840–849 (1992)] is initially effected by a family of membrane glycoproteins termed selections which are either expressed constitutively or induced in response to specific cytokines. Binding of selections to their counterpart ligand brings leukocytes into close, but not static, contact with vascular endothelial cells. The "tethered" leukocyte then begins a "rolling" process along the endothelium which continues until additional molecular interactions firmly stabilize a specific cell/cell interaction. One of the molecular binding activities which results in the stable interaction is effected by a second family of surface glycoproteins called integrins which possess a higher binding affinity for their respective ligands than selections.

The integrins are heterodimeric surface molecules comprised of an $\alpha$ and a $\beta$ subunit in non-covalent association. All integrins are transmembrane proteins with counter-receptor binding activity localized in the extracellular domain. Integrins also possess relatively short cytoplasmic regions which participate in transmembrane signaling events. Integrins are capable of interacting with other cell-bound counter-receptors and components of the extracellular matrix, as well as soluble factors. Binding of extracellular ligands leads to crosslinking and localized clustering of integrins [Miyamoto, et al., *Science* 267:833, 1995] and formation of focal adhesions wherein the clustered integrin cytoplasmic domains associate with cytoskeletal components including, for example, actin filaments [Pavalko and Otey, *Proc. Soc. Exp. Biol. Med.* 205:32767, 1994, and Gumbiner, *Neuron* 11:551, 1993]. While most investigations into integrin physiological activity have focused on identifying specific counter-receptors using immunological methodologies as discussed infra, less is known about the specific interactions of integrins with cytoplasmic components. Mutation studies, however, have indicated that the cytoplasmic sequences are required for integrin association with focal contacts [LaFlamme, et al., *J. Cell. Biol.* 117:437 (1992)]. Other data discussed infra support this observation.

While numerous integrins have been identified, certain subsets are unique to leukocytes, with each member of the subset having characteristic cell-specific expression and counter-receptor binding properties. Of leukocyte-specific integrins, at least three $\beta_2$ integrins are known, each comprised of a unique $\alpha$ subunit in association with a $\beta_2$ subunit (designated CD18) [Kishimoto, et al., *Cell* 48:681–690 (1987)]. For a recent review of the state of the art with regard to $\beta_2$ integrins, see Springer, *Cell* 76:301–314 (1994). CD11a/CD18, also known as $\alpha_L\beta_2$ or LFA-1, is expressed on all leukocytes and has been shown to bind to ICAM-1, ICAM-2, and ICAM-3. CD11b/CD18, also know as $\alpha_M\beta_2$ or Mac-1, is expressed on polymorphonuclear neutrophils, monocytes and eosinophils and has been shown to bind to ICAM-1, complement factor iC3b, factor X, and fibrinogen. CD11c/CD18, also known as $\alpha_X\beta_2$ or p150,95, is expressed on monocytes, polymorphonuclear neutrophils and eosinophils and has been shown to bind to complement factor iC3b and fibrinogen. In addition, a fourth human $\beta_2$ integrin, designated $\alpha_{d\beta 2}$, has recently been identified [Van der Vieren, et al., *Immunity* 3:683–690 (1995)]. Recently, it has been demonstrated that the actin-binding protein, filamin, directly binds to a cytoplasmic portion of $\beta_2$ subunits [Sharma, et al., *J. Immunol.* 154:3461–3470 (1995)] which suggests a role one or more of for the $\beta_2$ integrins in formation of focal contacts and cell motility in general [see review in Arnaout, *Blood* 75:1037 (1990)].

A second subset of leukocyte specific integrins may be referred to as the $\alpha_4$ integrins in view of the fact that both members of the family are comprised of a common $\alpha_4$ subunit in association with either a $\beta_1$ or $\beta_7$ subunit. For a recent review, see Springer, supra. VLA-4, also referred to as $\alpha_4\beta_1$ or CD49d/CD29, is expressed on most peripheral blood leukocytes except neutrophils and specifically binds VCAM-1 and fibronectin. LPAM-1, also known as $\alpha_4\beta_7$, is expressed on all peripheral blood leukocytes and has been shown to bind MadCAM-1, fibronectin and VCAM-1. Expression of either of the $\alpha_4$ integrins has also been demonstrated in a wide range of leukocyte cell types in lymphoid organs and in various tissues (Hemler et al., *Immunol. Rev.* 114:45–60, 1990; Kilshaw et al., *Eur. J. Immunol.* 20:2201–2207, 1990; Schweighoffer et al., *J. Immunol.* 151:717–729, 1993; and Lazarovits and Karsh, *J. Immunol.* 151:6482–6489, 1993). Consistent with the observed participation of $\beta_2$ integrins in formation of focal contacts, presumably through filamin binding, it has previously been shown that cytoplasmic portions of $\beta_1$ integrins directly bind a-actinin in vitro. While this interaction has not been demonstrated in vivo, it suggests physiological involvement of $\beta_1$ integrins in cell mobility and/or maintenance of cell morphology [see review in Clark and Brugge, *Science* 268:233–238 (1995)].

A number of in vitro and in vivo studies utilizing anti-$\alpha_4$ monoclonal antibodies have indicated a role for the $\alpha_4$ integrins in various pathophysiological conditions [see review, Lobb and Hemler, *J. Clin. Invest.* 94:1722–1728 (1994)]. For example, several investigations have provided evidence that $\alpha_4$ integrins are involved in leukocyte emigration from peripheral blood into regions of inflammation (Weg, et al., *J. Exp. Med.* 177:561–566, 1992; Winn and Harlan, *J. Clin. Invest.* 92:1168–1173, 1993). These observations suggest that anti-$\alpha_4$ antibodies may be capable of ameliorating integrin-associated disease states, and this therapeutic potential has been demonstrated in several animal disease state models. For example, bolus injection of antibodies to $\alpha_4$ integrins delayed the onset of paralysis in rat and murine experimental allergic encephalomyelitis (Yednock, et al., *Nature* 356:63–66, 1992; Baron, et al., *J. Exp. Med.* 177:57–68, 1993). Prophylactic administration of anti-$\alpha_4$ antibodies reduced ear swelling in murine contact hypersensitivity models (Ferguson, et al., *J. Immunol.* 150:1172–1182, 1993; Nakajima, et al., *J. Exp. Med.* 179:1145–1154, 1994). Further, anti-$\alpha_4$ antibodies were shown to reduce infiltration of pancreatic islets and delay the onset of diabetes in non-obese diabetic mice which are prone to spontaneous development of type I diabetes (Yang, et al., *Proc. Natl. Acad. Sci.* (USA) 90:10494–10498. 1993; Burkly, et al., *Diabetes* 43:529–534, 1994; Baron, et al., *J.*

Clin. Invest. 93:1700–1708, 1994). Still other in vivo studies using anti-$\alpha_4$ antibodies suggest a role for $\alpha_4$ integrins in allergic lung inflammation (Pretolani, et al., *J. Exp. Med.* 180:795–805 (1994); Milne and Piper, *Br. J. Pharnacol.* 112:82Pa(Abstr), 1994); inflammatory bowel disease (Podolsky, et al., *J. Clin. Invest.* 92:372–380, 1993); cardiac allograft rejection (Paul, et al., *Transplantation* 55:1196–1199, 1993); acute nephrotoxic nephritis (Mulligan, et al., *J. Clin. Invest.* 91:577–587, 1993); and immune complex mediated lung injury (Mulligan, et al., *J. Immunol.* 159:2407–2417, 1993).

Thus there exists a need in the art to identify molecules which bind to and/or modulate the binding and/or signalling activities of the integrins and to develop methods by which these molecules can be identified. The methods, and the molecules thereby identified, will provide practical means for therapeutic intervention in o$\alpha_4$ integrin-mediated immune and inflammatory responses.

BRIEF DESCRIPTION OF THE INVENTION

In one aspect, the present invention provides novel purified and isolated polynucleotides (e.g., DNA and RNA transcripts, both sense and antisense stands) encoding a filamin-like $\beta_7$ integrin binding protein designated FLP-1, or variants thereof (i.e., deletion, addition or substitution analogs) which possess binding and/or immunological properties inherent to FLP-1. Preferred DNA molecules of the invention include cDNA, genomic DNA and wholly or partially chemically synthesized DNA molecules. A presently preferred polynucleotide is the DNA as set forth in SEQ ID NO: 1, encoding the polypeptide according to SEQ ID NO:2.

Preferred polynucleotides of the invention comprise the cDNA set out in SEQ ID NO: 1 and DNAs which hybridize to the non-coding strands thereof under stringent conditions or which would hybridize but for the redundancy of the genetic code. Exemplary stringent hybridization conditions are as follows: hybridization at 42° C. in 5× SSPE and a final wash at 65° C. in 0.2× SSC. It is understood by those of skill in the art that variation in these conditions occurs based on the length and GC nucleotide content of the sequences to be hybridized. Formulas standard in the art are appropriate for determining exact hybridization conditions. See Sambrook, et al., Eds. 9.47–9.51 in *Molecular Cloning*, Cold Spring Harbor Laboratory Press, Cold Spring Harbor, N.Y. (1989).

Also provided are recombinant plasmid and viral expression constructs which include FLP-1 encoding sequences, wherein the FLP-1 encoding sequence is operatively linked to a homologous or heterologous transcriptional regulatory element or elements.

As another aspect of the invention, prokaryotic or eukaryotic host cells, transformed or transfected with polynucleotide sequences of the invention, are provided which express FLP-1 polypeptides or variants thereof. Host cells of the invention are particularly useful for large scale production of FLP-1 polypeptides which can be isolated from the host cell itself or the medium in which the host cell is grown.

Also provided by the present invention are purified and isolated FLP-1 polypeptides, including fragments and variants thereof. Novel FLP-1 polypeptides of the invention may be isolated from natural sources, but along with FLP-1 variant polypeptides, are preferably produced by recombinant procedures involving host cells of the invention. Variant FLP-1 polypeptides, including fully glycosylated, partially glycosylated, and wholly de-glycosylated forms of the FLP-1 polypeptide may be generated, depending on the host cell selected for recombinant production and/or post-isolation processing. Additional variant FLP-1 polypeptides include water soluble and insoluble FLP-1 polypeptides and fragments thereof, analogs wherein one or more amino acids are deleted from, replaced in, or added to the preferred FLP-1 polypeptide, polypeptide analogs with equal or enhanced biological activities and/or immunological characteristics specific for FLP-1, and analogs with modified ligand binding and/or signal transducing capabilities. Fusion polypeptides are also provided wherein FLP-1 amino acid sequences are expressed contiguously with amino acid sequences derived from other polypeptides. Fusion polypeptides of the invention include those with modified biological, biochemical, and/or immunological properties in comparison to the preferred FLP-1 polypeptide.

Also contemplated by the present invention are antibodies and other peptide and non-peptide molecules which specifically bind to FLP-1. Binding molecules of this type are particularly useful for purifying FLP-1 polypeptides, identifying cell types which express FLP-1 polypeptides, and assaying for presence or absence of FLP-1 polypeptides in a fluid. Binding molecules are also useful for modulating (i.e., blocking, inhibiting, or stimulating) in vivo binding and/or signal transduction activities of FLP-1. Antibodies of the invention include monoclonal, polyclonal, and recombinant (i.e., humanized, chimeric, etc.) forms and fragments thereof.

Also contemplated by the invention are hybridomas which secrete monoclonal antibodies specifically immunoreactive with FLP-1. Likewise, cell types modified by recombinant means so as to express and/or secrete genetically engineered FLP-1 binding molecules are also comprehended.

Assays to identify FLP-1 binding molecules are also provided, including immobilized ligand binding assays, solution binding assays, scintillation proximity assays, two hybrid screening assays, immunological methodologies and the like. In addition to identifying FLP-1 binding molecules, the same or similar assays are useful for identification of molecules which modulate FLP-1 specific binding. For example, assays to identify modulators (i.e., activators or inhibitors) of FLP-1 specific binding can involve a) contacting FLP-1 or a fragment thereof, with $\beta_7$ integrin or a fragment thereof; b) measuring binding between FLP-1 or a fragment thereof, and $\beta_7$ integrin or a fragment thereof; c) measuring binding between FLP-1 or a fragment thereof, and $\beta_7$ integrin or a fragment thereof in the presence of a test compound, and d) comparing the measurement in step (b) and the measurement in step (c) wherein a decrease in binding in step (c) indicates the test compound in an inhibitor of binding, and an increase in binding in step (c) indicates the test compound is an activator of binding.

Variations on the method to identify modulators of FLP-1 binding can include scintillation proximity assays comprising the steps of immobilizing either FLP-1 or its binding partner on a solid support, wherein the solid support contains a fluorescent agent; modifying the non-immobilized binding partner to include a compound that can excite the immobilized fluorescent agent; contacting the non-immobilized binding partner with the immobilized binding partner; determining the level of light emission for the fluorescent agent; and repeating the procedure in the presence of a putative modulator of FLP-1 binding.

As still another variation of the method, a two hybrid system may be utilized to identify genes encoding potential modulators. In this system, an integrin is expressed in a host cell as a fusion protein with either a DNA binding domain or transactivation domain of a modular transcription factor. A binding partner protein is also expressed as a fusion protein with which ever transcription factor domain is not utilized with expression of the integrin fusion protein. Interaction of the two fusion proteins results in reconstitution of the holo-transcription factor and permits expression of a reporter gene with a promoter specific for the transcription factor. Use of this system in the presence or absence of library cDNA can permit identification of genes that encode proteins which modulate the degree of reporter gene expression.

Additional methods comprehended by the invention include immunological assays including radio-immuno assays, enzyme linked immunosorbent assays, sandwich assays and the like. Co-precipitation methods are also comprehended wherein an antibody immunospecific for one binding partner is utilized in a method in which the other binding partner is detectably labeled. Immunological assays may also include use of labeled antibodies specifically immunoreactive with a complex between the desired binding partners.

Numerous compounds are contemplated as being candidates for testing in methods of the invention. For example, antibody products which are immunoreactive with one binding partner and which modulate binding between the two molecules can be identified by the claimed method. Antibody products contemplated are monoclonal antibodies, and fragments thereof, humanized antibodies, and/or single chain antibodies. Other molecules which can be screened in the claimed method include peptides, small molecules and libraries composed of either of the same.

Modulators of $\beta_7$/FLP-1 and $\beta_7$/filamin interaction identified by the methods of the invention are utilized in vitro or in vivo to affect inflammatory processes involving leukocytes. In addition, modulating compounds which bind to either the $\beta_7$ integrin, filamin or FLP-1 are useful to monitor the level of its binding partner, either in a body fluid or biopsied tissue.

Those of ordinary skill in the art will readily appreciate that numerous variations of the claimed method are encompassed by the invention.

DETAILED DESCRIPTION OF THE INVENTION

The present invention is illustrated by the following examples relating to the isolation of a cDNA clone encoding FLP-1. Example 1 relates to identification of genes in a human B cell cDNA library that encode proteins which interact with $\beta_7$ integrin. Example 2 describes identification of genes in a human spleen cDNA library which encode proteins that interact with $\beta_7$ integrin. Example 3 addresses tissue specific expression of FLP-1. Example 4 describes specificity of interaction between filamin and $\beta_7$ and FLP-1 and $\beta7$ integrin. Example 5 describes localization of $B_7$ sequences required for filamin or FLP-1 binding. Example 6 relates to applications for modulators of $\beta_7$/filamin or $\beta_7$/FLP-1 interactions.

EXAMPLE 1
Identification of Genes in a B Cell Library Encoding $\beta_7$ Interacting Proteins The two-hybrid system developed in yeast [Durfee, et al., *Genes and Development* 7:555–567 (1993)] was used to screen for proteins expressed in a human B cell cDNA library which interact with the carboxy-terminal cytoplasmic tail of the $\beta_7$ integrin. The yeast two-hybrid screen is based on in vivo reconstitution of the GAL4 transcription factor and subsequent expression of a reporter gene driven by a GAL4 promoter. Briefly, GAL4 DNA-binding and transcription-activating domains are encoded on separate plasmids as portions of fusion proteins. Expression of the fusion proteins and interaction of the expression products results in association of the two GAL4 domains and ultimate expression the $\beta$-galactosidase reporter gene under transcriptional control of the GAL4 promoter.

In the present investigation, a "bait" plasmid (pAS1) was constructed that contained sequences encoding the GAL4-binding domain, a trp⁻ selection requirement, a hemagglutinin (HA) epitope tag and cytoplasmic amino acid sequences of $\beta_7$ integrin. The $\beta_7$ integrin cytoplasmic domain was amplified by PCR using $\beta_7$ primers set out in SEQ ID NO:3 and 4.

NHβ₇5 CGGATCCTCGGATACCGGCTCTCGGTGAAG (SEQ ID NO: 3)
NHβ₇3 CGGCTCCTCAGAGAGTGGGACTGTCTGCCT (SEQ ID NO: 4)

Reaction conditions included an initial incubation at 94° C. for four minutes, followed by thirty cycles of: 94° C. for one minute, 50° C. for two minutes, and 72° C. for four minutes. The resulting product was sequenced to rule out PCR-derived errors and subcloned into vector pAS1. A yeast strain, Y190, was transformed with $\beta_7$/pAS1 by standard methods and grown in selective media (trp⁻) to mid-log phase. Cells were lysed in lysis buffer (containing 100 mM Tris, pH 6.8, 2% SDS, 10% glycerol, 5% BME and 0.1% bromo phenol blue) and the equivalent of 5–6×10⁶ cells of protein was separated on a 12% polyacrylamide gel. Proteins in the gel were transferred to a PVDF (Millipore, Bedford, Mass.) membrane by standard methods. Control lanes on the gel contained lysate from Y190 cells transformed with pASI vector alone (containing no $\beta_7$ integrin-encoding sequences). Western blotting was performed using antibody 12CA5, immunospecific for the HA epitope tag, (Boehringer Mannheim, Indianapolis, Ind.) and a goat anti-mouse IgG horse radish peroxidase (HRP) secondary antibody. Results, in combination with size determination using SDS-PAGE, confirmed that the fusion protein $\beta_7$ integrin cytoplasmic tail/HA/GAL4 DNA-binding domain was expressed at readily detectable levels.

A "target" vector was constructed with vector pACT modified to contain sequences encoding the GAL4 activation domain II fused to a B cell cDNA library and a leu⁻ selection requirement. Lymphocyte cDNA library sequences were inserted at an XhoI site of the vector. $\beta_7$/pAS1-transformed Y190 cells were transformed by standard methods with the pACT-lymphocyte library DNA and cells grown under selective conditions (leu⁻/trp⁻/his⁻/3-aminotriazole). Resulting colonies were tested for $\beta$-galactosidase ($\beta$-gal) activity by the blue/white selection method well known in the art and forty-four $\beta$-gal positive clones were obtained. Sequence analysis of the B cell cDNA-derived pACT inserts in each of the clones revealed twenty novel sequences and twenty four sequences encoding known proteins or portions of known proteins.

Five clones were of particular interest, all of which contained sequences encoding a portion of the non-muscle protein filamin, or actin-binding protein ABP280(emb/X53416), [Gorlin, et al., *J. Cell Biol.* 111: 1089–1105 (1990)]. All five clones were shown to encode the carboxy-terminal portions of filamin (SEQ ID NO: 7) and each clone extended into 3' untranslated portions of the filamin gene. Clone 411 corresponded to sequences in repeat 20 (beginning at nucleotide 6763 in SEQ ID NO: 7) and clones 514, 1521, 1271 and 722 beginning in repeat 23 (each beginning at nucleotide 7513, 7552, 7579, and 7579 in SEQ ID NO: 7, respectively). There was one discrepancy between the published sequence of filamin and the sequences determined in each of the positive clones: all positive clones had an aspartate residue at position 2634, while the published sequence of filamin had a histidine at that position. Of these clones, 1271 was selected for subsequent analysis, and the nucleotide and amino acids sequences of 1271 are set out in SEQ ID NOs: 5 and 6, respectively.

EXAMPLE 2

Identification of Genes in a Human Spleen Library Encoding $\beta_7$ Interacting Proteins The two-hybrid system described in Example 1 was repeated using human spleen cDNA library sequences (Clontech, Palo Alto, Calif.) cloned into an EcoRI site of the target vector pGAD10 (Clontech).

After transformation of the $\beta_7$/pAS1 Y190 strain with the spleen/pGAD10 plasmid and selection as previously described, the resulting colonies were tested for β-gal activity and six positive clones were identified. Sequence analysis of the six β-gal positive clones that revealed five identical clones (from which clone S5 was selected for further analysis) along with clone S3, (the sixth positive clone and distinct from the other five) were identified.

DNA and protein alignments revealed that clones S3 and S5 encode different, but overlapping regions of the same protein, with the S3 insert beginning 5' of the S5 insert, and terminating before the 3' end of clone S5. The DNA sequences of clones S3 and S5 were compared to DNA databases using NCBI Blastn with default parameters on Oct. 16, 1995, and both clones were found to exhibit approximately 70% identity to filamin. The nucleotide and amino acid sequences of clone S3 are set out in SEQ ID NOs: 9 and 10, respectively. Sequences for clone S5 are set out in SEQ ID NOs: 11 and 12, respectively. The composite protein encoded by the overlapping clones S3 and S5 was designated FLP-1 (filamin like protein). Blastp search of protein database (NCBI Blastp) revealed that the composite protein FLP-1 has a 73% identity to filamin. Alignment of FLP-I to filamin shows that clones S3 and S5 represent carboxy terminal regions of FLP-1. When FLP-1 is aligned with filamin in the second hinge region between repeats 23 and 24, the putative glycoprotein binding region, the degree of identity drops to 38%, suggesting a difference in binding affinity between filamin and FLP-1 for membrane glycoproteins.

In addition, a region of clone S5 was further found to exhibit 100% identity to truncated actin-binding protein TABP (GP or GE/M62994), a protein previously shown to be is a truncated, non-actin-binding filamin-like protein [Leedman, et al., *Proc. Natl.Acad. Sci. (USA)* 90:5994–5998 (1993)] having 195 amino acids and a molecular weight of approximately 21 kDa. Identity was particularly high between nucleotides 950–1515 of clone 5 which were 95–99% identical to regions of TABP. TABP lacks an actin binding domain and 22 of 24 tandem repeats found in filamin, but contains sequences homologous to the carboxy terminal repeats numbered 23 and 24 found in filamin. The TABP hinge region, between repeats 23 and 24, contains a putative glycoprotein binding site and a $Ca^{2+}$/calmodulin kinase II phosphorylation site [Leedman, supra]. TABP is encoded by a 2.3 kb mRNA and a CDNA encoding TABP was cloned from a thyroid expression library from a Graves disease patient [Leedmen, supra].

In order to obtain a more complete FLP-1 sequence, the human spleen cDNA library was screened using S3 as a probe. The S3 clone was digested with EcoRI and a 1.2 kb fragment was isolated and labeled using the Random Primed Labeling Kit (Boehringer Mannheim, Indianapolis, Ind.) according to the manufacturer's suggested protocol. Unincorporated nucleotides were removed using a Centrisep column (Princeton Separations, Adelphia, N.J.). The probe was added to filters in hybridization solution (5× SSPE, 45% formamide, 5× Denhardts, 1% SDS) and hybridized overnight at 42° C. The filters were washed at a final stringency of 0.2× SSC/0.1% SDS at 65° C.

Primary positive clones were picked, diluted and replated on Hybond N$^+$ filters on LBM plates. Two duplicate filters were rehybridized with hybridization solution saved from the original hybridization described supra. Clones which were positive on both filters were picked, grown and their plasmids isolated and sequenced by standard methods.

Ten FLP-1 positive clones were detected and sequence data from these clones was compared to filamin and FLP-1 sequences derived from clone S3 and S5. Overlap of sequences from clones S3 and S5 with sequences from clones F3, F5 and F7 permitted determination of a more complete sequence for FLP-1, the more complete nucleotide and amino acid sequences set out in SEQ ID NOs: 1 and 2, respectively. In SEQ ID NO: 1, nucleotides 1–315 were derived from clone F5; nucleotides 316–738 from clone F3; nucleotides 739–816 from clone F7; nucleotides 817–1122 from clone S3 and nucleotides 1123–2574 from clone S5.

EXAMPLE 3

Tissue Specific Expression of FLP-1

In order to determine size of a mRNA encoding FLP-1 in various tissues, a human immune system multiple tissue northern (Clontech) was probed with a random-primed portion of clone S3 (corresponding to nucleotides 255–777 in SEQ ID NO: 9) according to manufacturer's suggested protocol.

In spleen, lymph node, thymus, bone marrow, and fetal liver, mRNA of two distinct sizes hybridized to the FLP-1 probe: one just above and one just below the 9.5Kb size marker. In appendix and peripheral blood leukocytes, only one band, just below the 9.5Kb size marker, hybridized with the FLP-1 probe. These results suggest that the FLP-1 mRNA encodes a protein similar in size to filamin as reported in Gorlin, supra.

EXAMPLE 4

Specificity of Filamin/$\beta_7$ and FLP-1/$\beta_7$ Interaction

The specificity of the interactions of filamin and FLP-1 with the $\beta_7$ integrin cytoplasmic tail was verified by transforming filamin clone 1271 and FLP-1 clone S5 into Y190 strains containing any one of a variety of "baits" vectors (encoding either $\beta_1$, $\beta_2$, $\beta_7$ $\alpha_L$, or $\alpha_4$ integrin cytoplasmic tails) using standard methods described supra. Results from this assay, shown in Table 1, indicated that filamin and FLP-1 specifically bind to $\beta_7$ integrins and not to other integrins.

TABLE 1

Binding Specificity of Filamin and FLP-1
SPECIFICITY OF INTERACTION

| INTEGRIN "BAIT" | FILAMIN | FLP-1 |
|---|---|---|
| $\beta_1$ | − | − |
| $\beta_2$ | − | − |
| $\beta_7$ | + | + |

TABLE 1-continued

Binding Specificity of Filamin and FLP-1
SPECIFICITY OF INTERACTION

| INTEGRIN "BAIT" | FILAMIN | FLP-1 |
|---|---|---|
| $\alpha_L$ | – | – |
| $\alpha_4$ | – | – |

In vivo interaction between filamin and $\beta_7$ integrin was also investigated by co-precipitation of a filamin/$\alpha_4\beta_7$ complex from JY cells, which express endogenous $\alpha_4\beta_7$-Cells were initially permeabilized with 10 µg/ml lysolecithin (Sigma, St. Louis, Mo.) in PBS, pH 8.0, with 1 mM $Ca^{++}$ and 1 mM $Mg^{++}$, for five minutes. Cellular proteins were crosslinked using DTSSP (921 µM) and labeled with biotin as described in Altin, et al., *Anal. Biochem.* 224:382–389 (1995). Crosslinked cells were lysed using 1% Triton-X100 and integrins were immunoprecipated using monoclonal antibodies immunospecific for $\alpha_4$ (antibody HP2/1, Immunotech, Westbrook, Me., or antibody B5G10, Upstate Biotechnology, Inc., Lake Placid, N.Y.), or $\beta_2$ (antibody 23 IIIb). A control antibody, PC21 (Sigma, St. Louis, Mo.) was also employed. Precipitated proteins were separated on a 6% SDS-PAGE gel, transferred to an Immobilon P membrane and probed with filamin antisera (Chemicon International, Inc. Temecula, Calif.).

Consistent with the hybrid screen, results demonstrate filamin co-precipitation with an $\alpha_4$ integrin, however in this assay, full length filamin also co-precipitated with the $\beta_2$ subunit.

EXAMPLE 5

Localization of FLP-1 or Filamin Binding on $\beta_7$

In order to more fully characterize the binding between FLP-1 or filamin and $\beta_7$ integrin, the two-hybrid assay was employed using various deletion derivatives of either of the individual binding partners.

Several cytoplasmic domain mutants of the $\beta_7$ integrin were created using PCR in order to map the site(s) of interaction observed as described above. Filamin clone 1271 and FLP-1 clone S5 were employed to evaluate the degree to which mutations in the $\beta_7$ cytoplasmic domain affected binding. Following standard co-transformations of Y190 as described above, binding interactions were determined by $\beta$-gal assay, as described above. The $\beta_7$ deletions and substitutions are set out in SEQ ID NOS: 14 to 18 below, and compared to the native $\beta_7$ sequence set out in SEQ ID NO: 13. In each expression construct, only the cytoplasmic portion of $\beta_7$, or a truncation thereof, was subcloned.

| | | |
|---|---|---|
| $\beta_7$ | RLSVEIYDRREYSRFEKEQQQLNWKQDSNPLYKSAITTTINPRFQEADSPTL | (SEQ ID NO: 13) |
| $\beta_7$D1 | RLSVEIYDRREYSRFEKEQQQLNWKQDSNP | (SEQ ID NO: 14) |
| $\beta_7$D2 | RLSVEIYDRREYSRFEKEQQQLNWKQDSNPLYKSA | (SEQ ID NO: 15) |
| $\beta_7$D3 | RLSVEIYDRREYSRFEKEQQQLNWKQDSNPLYKSAITTTINP | (SEQ ID NO: 16) |
| $\beta_7$D4 | RLSVEIYDRREYSRFEKE | (SEQ ID NO: 17) |
| $\beta_7$D5 | RLSVEIYDRREYSR | (SEQ ID NO: 18) |

Primers used to generate the various deletion mutants are set out in SEQ ID NOs: 19 to 23, below, and were individually utilized in an amplification reaction pairs with the primer set out in SEQ ID NO: 3. Reaction conditions were as described in Example 1.

| | | |
|---|---|---|
| NH$\beta_7$D1 | GATGGCACTTTTGTACTAAGGATTACTGTCCTG | (SEQ ID NO: 19) |
| NH$\beta_7$D2 | ATTGATGGTGGTCGTCTAGGCACTTTTGTAGAG | (SEQ ID NO: 20) |
| NH$\beta_7$D3 | GTCTGCCTCTTGAAACTAAGGATTGATGGTGGT | (SEQ ID NO: 21) |
| NH$\beta_7$D4 | CCAGTTGAGTTGTTGCTACTCCTTCTCAAAGCG | (SEQ ID NO: 22) |
| NH$\beta_7$D5 | GTTGCTGCTCCTTCTCCTAGCGACTGTATTCCCG | (SEQ ID NO: 23) |

In addition, a series of $\beta_7$ substitution mutants were also constructed wherein the sequence changes are set out in SEQ ID NOs: 24 to 27, with the substituted amino acid residue underlined.

| | | |
|---|---|---|
| $\beta_7$S3A | RL<u>A</u>VEIYDRREYSRFEKEQQQLNWKQDSNPLYKSAITTTINPRFQEADSPTL | (SEQ ID NO: 24) |
| $\beta_7$E5Q | RLSV<u>Q</u>IYDRREYSRFEKEQQQLNWKQDSNPLYKSAITTTINPRFQEADSPTL | (SEQ ID NO: 25) |
| $\beta_7$R9A | RLSVEIYD<u>A</u>REYSRFEKEQQQLNWKQDSNPLYKSAITTTINPRFQEADSPTL | (SEQ ID NO: 26) |
| $\beta_7$S13A | RLSVEIYDRREY<u>A</u>RFEKEQQQLNWKQDSNPLYKSAITTTINPRFQEADSPTL | (SEQ ID NO: 27) |

Oligonucleotides used to generate the various substitution variants are set out in SEQ ID NOs: 28 to 31, infra.

| | | |
|---|---|---|
| B7S3A | GTCATAGATTTCCACCGCGAGCCGGTATCCGAG | (SEQ ID NO: 28) |
| B7E5Q | CCGGCCGTCATAGATTTGCACCGAGAGCCGGTATC | (SEQ ID NO: 29) |
| B7R9A | GCGACTGTATTCCCGCGCGTCATAGATTTCCAC | (SEQ ID NO: 30) |
| B7S13A | CTCCTTCTCAAAGCGCGCGTATTCCCGGCGGTC | (SEQ ID NO: 31) |

Specific truncation mutants of filamin were generated by PCR amplification of existing clones under conditions described in Example 1. Mutant ABPD1 encoded a region including an actin binding domain and a dimerization domain of filamin (amino acid 2487–2644 in SEQ ID NO: 7). Mutant ABPD2 encoded a truncated form of ABPD1 which lacked the filamin dimerization domain (amino acids 2487–2577 in SEQ ID NO: 7). Both mutants were generated by PCR using primers set out in SEQ ID NO: 32 and 33 to generate mutant ABPD1, and primers set out in SEQ ID NO: 32 and 34 to generate ABPD2.

| | | |
|---|---|---|
| ABP.5x | ATATCTCGAGAGTATACCCCCATGGCACCT | (SEQ ID NO: 32) |
| ABP.Xho1 | ATATCTCGAGTCAGGGCACCACAACGCG | (SEQ ID NO: 33) |
| ABP.Xho2 | ATATCTCGAGTCAGCTGCTCTTCTGGCCCTAC | (SEQ ID NO: 34) |

Primers as described were used in a reaction with filamin clone 1271 under the following amplification conditions: an initial incubation at 94° C. for five minutes, followed by thirty cycles of 94° C. for 30 seconds, 50° C. for 30 seconds, and 72° C. for one minute. The resulting PCR product was cut with Xho1 and ligated into vector pACT (described in Example 1) previously digested with Xho1.

An FLP-1 mutant comprised of amino acid sequences 696 to 857 in SEQ ID NO: 1 and showing identity to TABP (the TABP-like analog) was also generated by PCR amplification (under conditions described in Example 1) from a human spleen cDNA library. The FLP-1 mutant was generated by PCR using the primer pair set out in SEQ ID NO: 35 and 36.

| | | |
|---|---|---|
| TABP.Nde | ATATCATATGTACACCCCCATGGCTCCT | (SEQ ID NO: 35) |
| TABP.Bam | ATAGGATCCTCAGCCCCACAAACAGGC | (SEQ ID NO: 36) |

Reactions were carried out using 2.5 μg spleen cDNA under the following amplification conditions: an initial incubation at 94° C. for five minutes, followed by thirty cycles of 94° C. for 30 seconds, 50° C. for 30 seconds, and 72° C. for one minute. The resulting PCR products were digested with NdeI and BamHi and cloned into vector pET previously digested with the same enzymes. The resulting TABP/pET vector was then utilized in a secondary PCR with the PCR primer pair set out in SEQ ID NO: 32 and 33, above, under the following conditions: an initial incubation at 94° C. for five minutes, followed by thirty cycles at 94° C. for one minute, 50° C. for one minute and 72° C. for two minutes. The resulting PCR product was digested with Xho1 and cloned into pACT previously digested with Xho1. The FLP-1 TABP-like truncate represents the same size and region in filamin as represented by mutant ABPD1.

Results from the two hybrid assay as shown in Table 2 indicated that none of the $\beta_7$ cytoplasmic domain mutations completely disrupted interaction with either filamin clone 1271 or FLP-1 clone S5. The substitution mutant $\beta_7$E5Q however appeared to result in a weaker interaction with filamin clone 1271 and ABDP1. Removal of the 3' untranslated region in filamin mutant ABPD1 also did not disrupt the interaction with the $\beta_7$ cytoplasmic domain, but removal of the dimerization domain as in filamin mutant ABPD2 abolished filamin/$\beta_7$ interaction completely. These data indicate that the filamin dimerization region is critical for interaction with the $\beta_7$ cytoplasmic domain.

The FLP-1 TABP-like truncate failed to interact with the $\beta_7$ integrin cytoplasmic domain. In addition, none of the $\beta_7$ mutants disrupted detectable FLP-1/$\beta_7$ interaction.

TABLE 2

INTERACTION OF FILAMIN AND FLP-1 WITH $\beta_7$ DELETION AND SUBSTITUTION ANALOGS

| | FILAMIN | ABPD1 | ABPD2 | FLP-1 | TABP |
|---|---|---|---|---|---|
| $\beta_1$ | − | − | | − | − |
| $\beta_2$ | − | − | − | − | − |
| $\beta_7$ | + | +/− | − | + | − |
| $\beta_7$D1 | + | + | +/− | − | |
| $\beta_7$D2 | + | + | +/− | − | |
| $\beta_7$D3 | + | + | − | + | |
| $\beta_7$D4 | + | + | − | + | |
| $\beta_7$D5 | + | + | | + | |
| $\beta_7$S3A | + | + | | + | |
| $\beta_7$E5Q | +/− | +/− | | + | |
| $\beta_7$R9A | + | + | | + | |
| $\beta_7$S13A | + | + | | + | |
| $\alpha_L$ | − | | | − | − |
| $\alpha_4$ | − | | | − | − |

EXAMPLE 6
Applications for Modulators of Filamin/ß$_7$ and FLP-1/ß$_7$ Binding Two ß$_7$ associated integrins have been identified: α$_4$ß$_7$ and α$_E$ß$_7$. Both are expressed on a subpopulation of peripheral blood lymphocytes and their expression is inducible. Both are expressed on macrophages but not monocytes and both appear to function in homing or localization of lymphocytes to mucosal tissue [see review in Jutila, *J. Leukocyte Biol.* 55:133–140 (1994)]. The homing properties of α$_4$ß$_7$ can be attributed to interaction with MadCAM-1 expressed in mucosal nodes, while the retention of α$_E$ß$_7^+$ cells in the gut is attributed to interactions with epithelial cells expressing E-cadherin. Thus, binding by one or both ß$_7$ integrins to their respective counter-receptor may contribute to mucosal immune responses as well as inflammatory (e.g., inflammatory bowel disease, IBD) and autoimmune responses at this site.

Further, it has been suggested that filamin is important in cell locomotion due to the fact that cells expressing low levels of the protein do not form leading lamella structures required for locomotion. The structural homology of FLP-1 to filamin suggests a similar role for this protein. In view of the observation that integrins can be observed clustered in point contacts, which are also important in cell locomotion, the invention contemplates that ß$_7$ interaction with FLP-1 and/or filamin may be crucial to cell movement, and that disruption of the interactions will be useful, for example, in preventing the homing of $_7$$^+$ cells which occurs in certain pathological inflammatory responses such as IBD.

In order to identify modulators of ß$_7$/FLP-1 interaction, it is necessary to clearly define the portions of both proteins which are necessary for binding. Amino acid substitution, through standard mutagenesis techniques will permit identification of the binding regions of the proteins. Deletion analysis, wherein truncated forms of either protein are generated, for example by PCR, is also useful for identification of binding regions if the deletion does not disrupt the tertiary or quaternary structure of the protein to the point that it is no longer recognized buy its counter-receptor.

Identification of the significant protein regions involved in binding permits more accurate and efficient screening of putative modulators of binding activity. The invention contemplates of a high throughput screening assay to analyze large libraries of small molecules or peptides, as well as antibodies immunospecific for either or both binding partners, for the ability to modulate binding of ß$_7$ integrins to FLP-1 or filamin. While two hybrid screening, scintillation proximity assays (SPA) and immunological methodologies, for example, enzyme-linked immunosorbent assays (ELISA), disclosed herein are not HTS methods per se, they are amenable to test many of the compounds listed for an ability to modulate binding. SPA and ELISA are particularly useful in this identification process and can be modified to permit high throughput screening of the test compounds described.

What is claimed is:

1. A purified and isolated polynucleotide encoding the $\beta_7$ integrin cytoplasmic domain-binding human FLP-1 (Flamin-like binding proteins) amino acid sequence set out in SEQ ID NO: 2.

2. The polynucleotide of claim 1 which is a DNA molecule.

3. The polynucleotide of claim 2, wherein tne DNA molecule which is selected from the group consisting of cDNA, genomic DNA, partially chemically synthesized DNA, and wholly chemically synthesized DNA.

4. A purified and isolated DNA molecule consisting of the human FLP-1 polypeptide encoding sequence set out in SEQ ID: 1.

5. A purified and isolated DNA molecule encoding a $\beta_7$ integrin cytoplasmic domain-binding FLP-1 polypeptide selected from the group consisting of:

a) the human DNA sequence set out in SEQ ID NO: 1;

b) a DNA molecule which hybridizes under stringent conditions to the noncoding strand of the protein coding portion of (a); and c) a DNA molecule that would hybridize to the DNA of (a) but for the degeneracy of the genetic code.

6. A DNA expression construct comprising the DNA molecule of claim 4, or 5.

7. A host cell transformed or transfected with the expression construct of claim 6.

8. A method for producing a $\beta_7$ integrin cytoylasmic domain-binding FLP-1 polypeptide comprising growing the host cell of claim 7 in a suitable medium and isolating a FLP-1 polypeptide from the host cell or the medium of its growth.

* * * * *

UNITED STATES PATENT AND TRADEMARK OFFICE
CERTIFICATE OF CORRECTION

PATENT NO. : 5,922,570
DATED : July 13, 1999
INVENTOR(S) : Staunton et al.

It is certified that error appears in the above-identified patent and that said Letters Patent is hereby corrected as shown below:

Col. 2, line 9: Please delete "$\alpha_{d\beta2}$", and insert - -$\alpha_d\beta_2$- -.

Col. 2, line 37: Please delete "A-actinin", and insert - -$\alpha$-actinin- -.

Col. 3, line 4: Please delete "Pharnacol", and insert -Pharmacol-.

Col 3, line 17: Please delete "o$\alpha_4$", and insert - -$\alpha_4$- -.

Col 3, line 24: Please delete "stands", and insert - -strands- -

Col 7, line 41: Please delete "FLP-I", and insert - -FLP-1- -.

Col. 9 line 13: After $\alpha_4\beta_7$ please delete "-", and insert - -,- -.

Col. 11, line 17: Please delete "NO", and insert - -$NO_S$- -.

Col. 11, line 18: Please delete "NO", and insert - -$NO_S$- -.

Col. 11, line 39: Please delete "NO", and insert - -$NO_S$- -.

Col. 11, line 54: Please delete "NO", and insert - -$NO_S$- -.

Col. 12, Table 2, $B_7D1$, Column ABPD-2: Please delete "+/-" and insert - - ---.

Col. 12, Table 2, $B_7D1$, Column FLP-1: Please delete "-" and insert - -+/-- -.

Col. 12, Table 2, $B_7D2$, Column ABPD-2: Please delete "+/-" and insert - - ---.

Col. 12, Table 2, $B_7D2$, Column FLP-1: Please delete "-" and insert - -+/-- -.

Col. 13, line 2: Please delete "Filamin/fi$_7$", please insert --Filamin/$\beta_7$--.

UNITED STATES PATENT AND TRADEMARK OFFICE
CERTIFICATE OF CORRECTION

PATENT NO. : 5,922,570
DATED : July 13, 1999
INVENTOR(S) : Staunton et al.

It is certified that error appears in the above-identified patent and that said Letters Patent is hereby corrected as shown below:

Col. 14, line 1: Please delete "$_7^+$", and insert --$\beta_7^+$--.

Col. 14, line 12: Please delete "buy", and insert --by--.

Col. 77, line 39: Please delete "Flamin-like", and insert --Filamin-like--.

Signed and Sealed this

Twenty-fourth Day of April, 2001

Attest:

NICHOLAS P. GODICI

Attesting Officer

Acting Director of the United States Patent and Trademark Office